United States Patent
Li et al.

(10) Patent No.: US 9,351,946 B2
(45) Date of Patent: May 31, 2016

(54) MTOR-INDEPENDENT ACTIVATOR OF TFEB FOR AUTOPHAGY ENHANCEMENT AND USES THEREOF

(71) Applicant: Hong Kong Baptist University, Hong Kong (HK)

(72) Inventors: Min Li, Hong Kong (HK); Juxian Song, Hong Kong (HK); Yu Zeng, Hong Kong (HK); Liangfeng Liu, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 0 days.

(21) Appl. No.: 14/609,438

(22) Filed: Jan. 30, 2015

(65) Prior Publication Data
US 2015/0250741 A1   Sep. 10, 2015

Related U.S. Application Data

(60) Provisional application No. 61/949,233, filed on Mar. 6, 2014.

(51) Int. Cl.
*A61K 31/12* (2006.01)

(52) U.S. Cl.
CPC ..................... *A61K 31/12* (2013.01)

(58) Field of Classification Search
None
See application file for complete search history.

(56) References Cited

U.S. PATENT DOCUMENTS

2007/0060644 A1    3/2007   Vander Jagt et al.

FOREIGN PATENT DOCUMENTS

| | | |
|---|---|---|
| CN | 102225919 A | 10/2011 |
| CN | 102670573 A | 9/2012 |
| WO | 2012021692 A1 | 2/2012 |

OTHER PUBLICATIONS

CAPLUS 2012:1387507.*
Yang, D.-S. et al., Brain 2011, vol. 134, pp. 258-277.*
Orlando, D.A. et al. A chemical analog of curcumin as an improved inhibitor of amyloid abeta oligomerization Plos one Mar. 19, 2012 Issue 3 vol. 7.
International search report of PCT application No. PCT/CN2015/073764 issued from the International Search Authority on Jul. 31, 2015.
Settembre, C., et. al., TFEB links autophagy to lysosomal biogenesis. Science, 2011. 332(6036): 1429-33.
Reagan-Shaw S1, et. al., Dose translation from animal to human studies revisited. FASEB J. 2008;22(3):659-61.
Sardiello, M., et al., A gene network regulating lysosomal biogenesis and function. Science, 2009. 325(5939): 473-7.

* cited by examiner

*Primary Examiner* — Heidi Reese
(74) *Attorney, Agent, or Firm* — Ella Cheong Hong Kong; Sam T. Yip

(57) ABSTRACT

The present invention relates to a composition comprising an autophagy enhancement compound. Small molecules that are able to enhance autophagy and lysosome biogenesis by activating the gene TFEB which can prevent the accumulation of toxic protein aggregates in treating neurodegenerative diseases are disclosed.

17 Claims, 22 Drawing Sheets

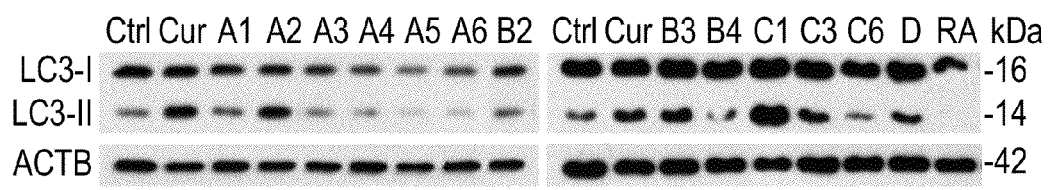
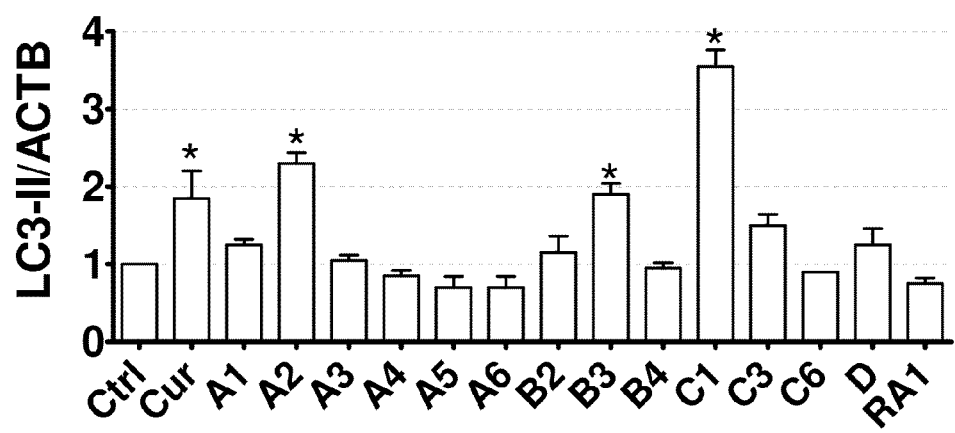
Fig. 2A
Fig. 2

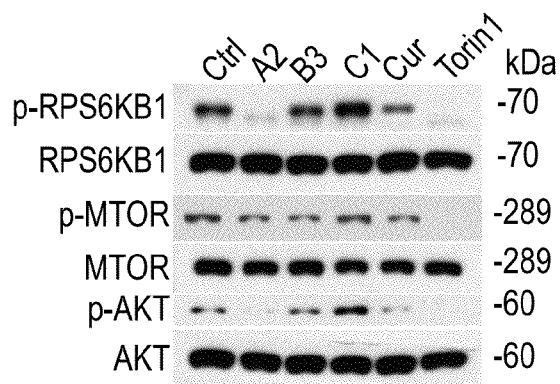
Fig. 3A
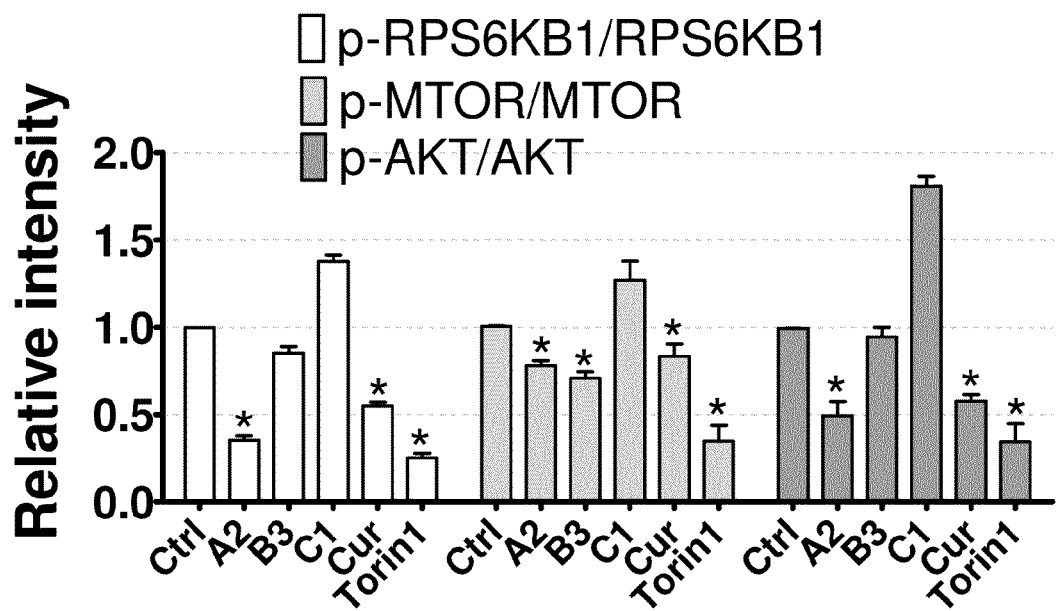
Fig. 3B
Fig. 3

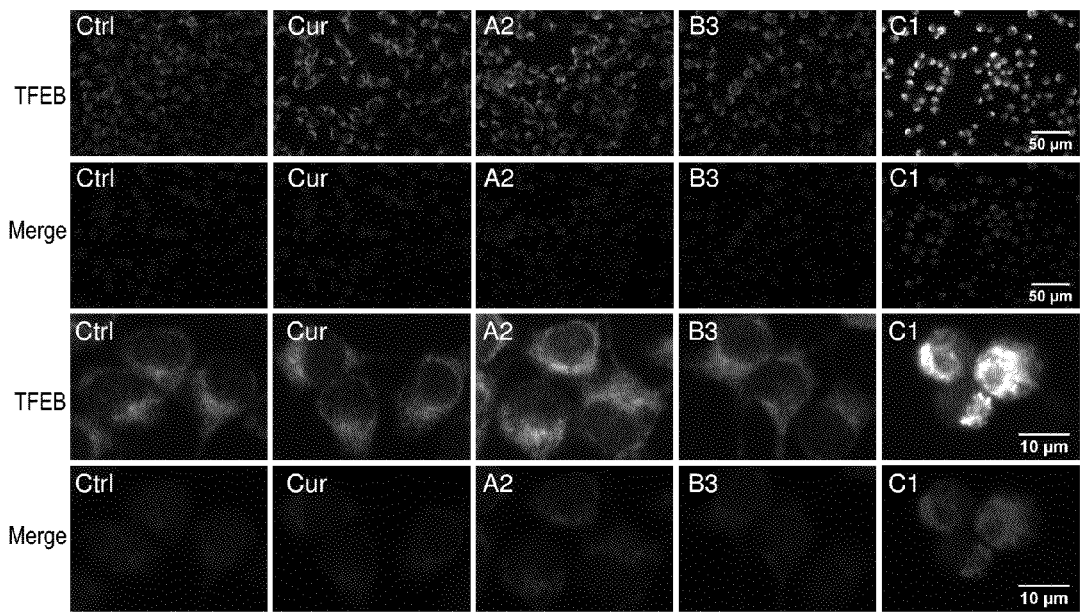
Fig. 4A
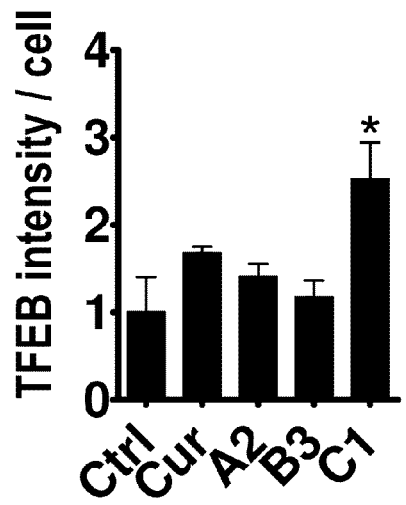
Fig. 4B
Fig. 4

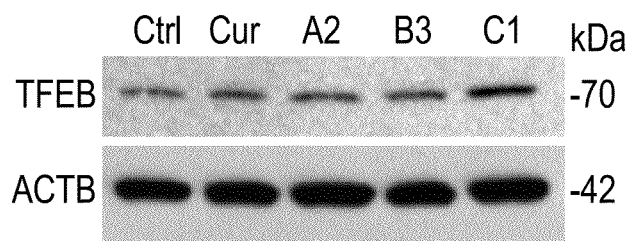
Fig. 4C
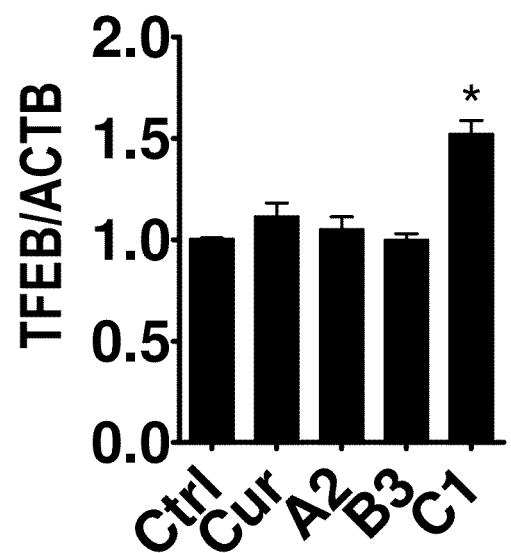
Fig. 4D
Fig. 4

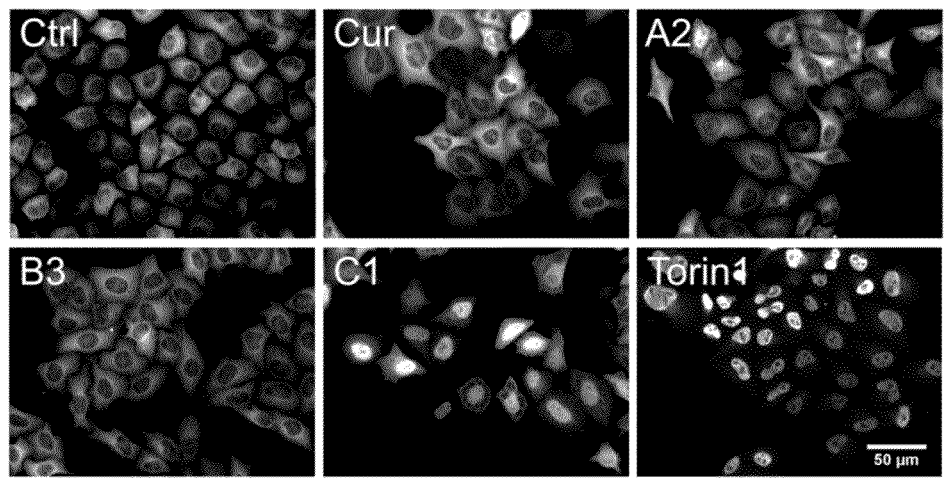
Fig. 4E
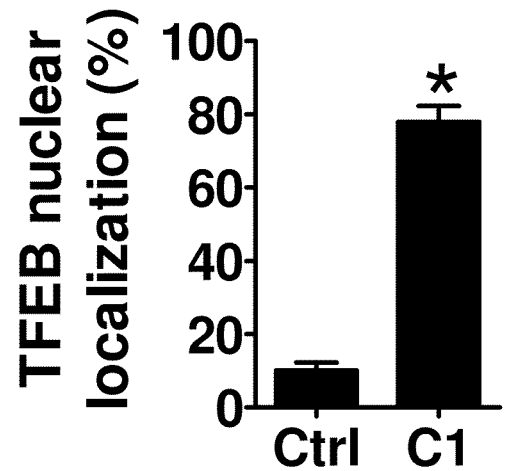
Fig. 4F
Fig. 4

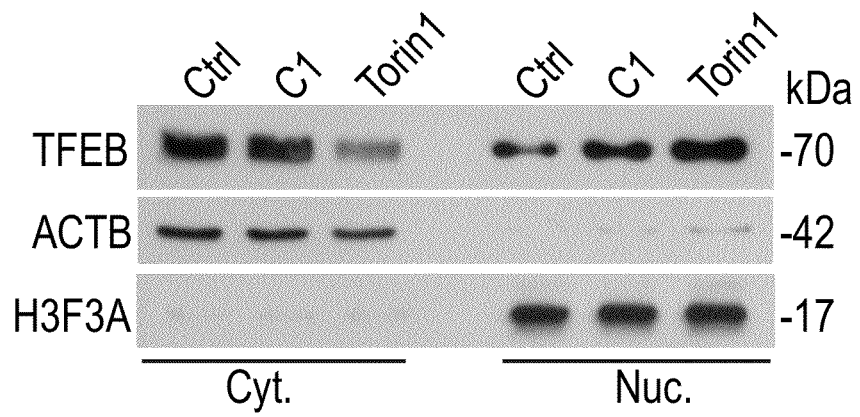
Fig. 4G
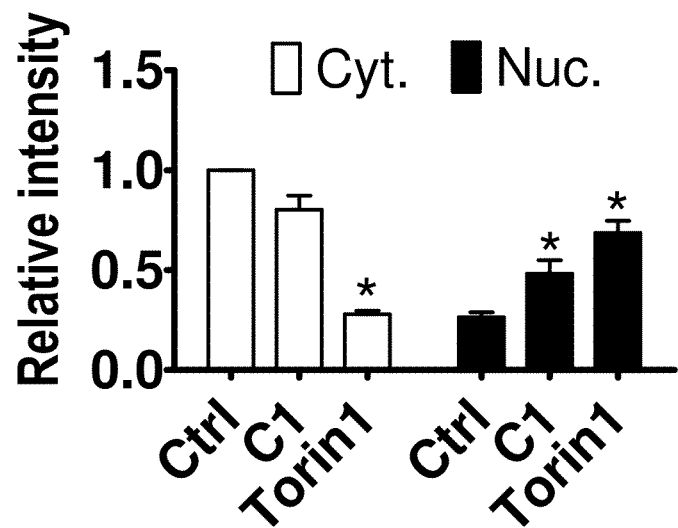
Fig. 4H
Fig. 4

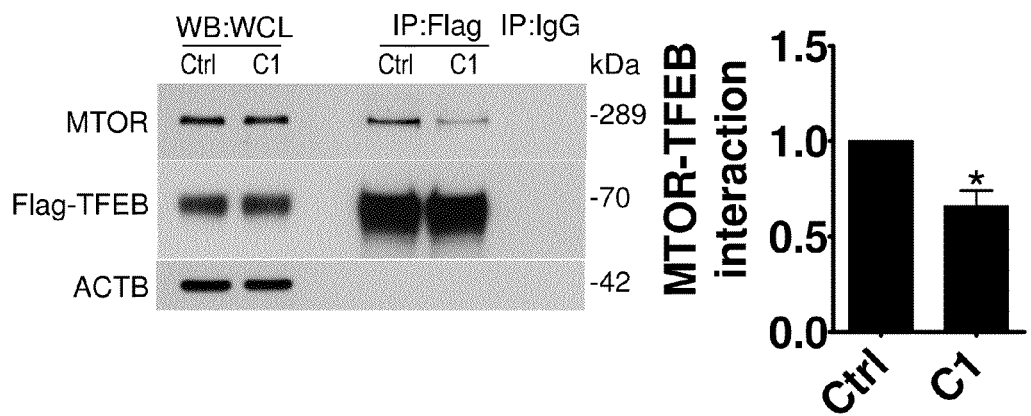
Fig. 5A
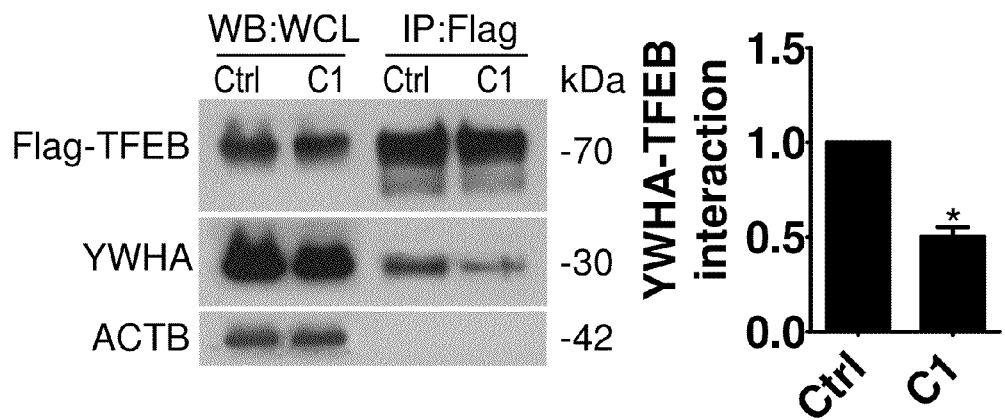
Fig. 5B
Fig. 5

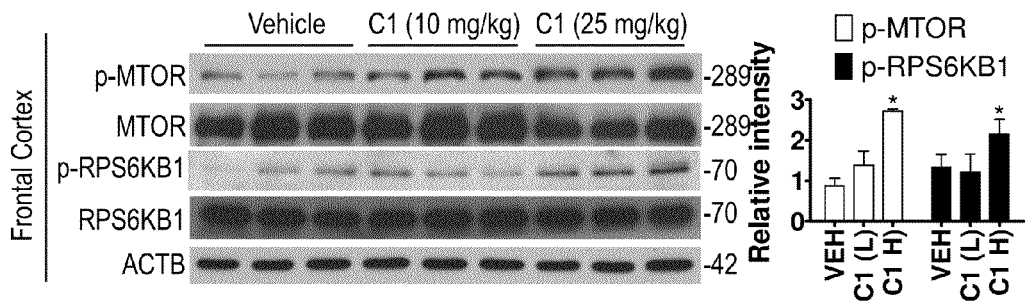
Fig. 10A
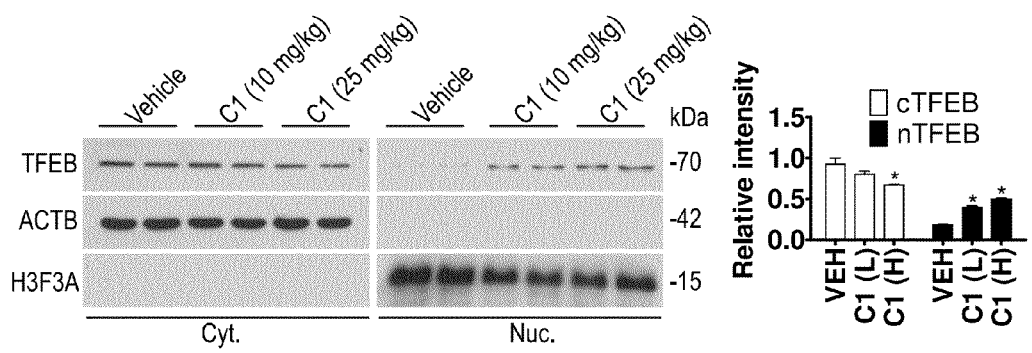
Fig. 10B
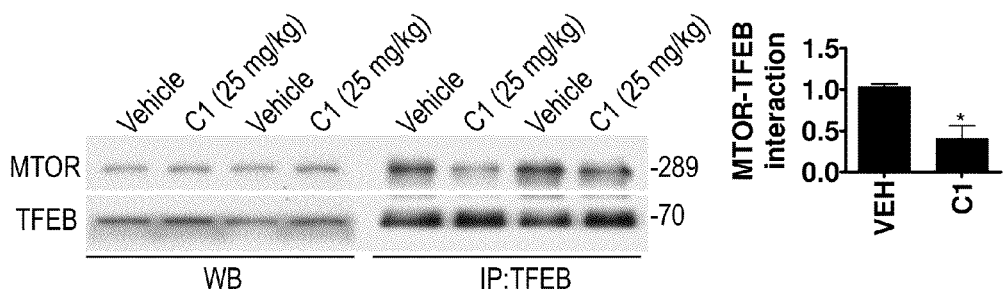
Fig. 10C
Fig. 10

MTOR-INDEPENDENT ACTIVATOR OF TFEB FOR AUTOPHAGY ENHANCEMENT AND USES THEREOF

CROSS-REFERENCE TO RELATED APPLICATIONS

This application claims the benefit of U.S. Provisional Patent Application Ser. No. 61/949,233 filed on Mar. 6, 2014, the disclosure of which is hereby incorporated by reference.

FIELD OF INVENTION

The present invention relates to a composition comprising an autophagy enhancement compound. In particular, the present invention relates to a composition comprising a small molecule being able to enhance autophagy and lysosome biogenesis by activating the gene TFEB which can prevent the accumulation of toxic protein aggregates in treating neurodegenerative diseases such as Parkinson's, Alzheimer's and Huntington's diseases.

BACKGROUND OF INVENTION

Macroautophagy, herein referred to as autophagy, is a highly conserved process for cellular degradation and recycling of cytosolic contents to maintain cellular homeostasis. Autophagy substrates are generally cellular organelles, long-lived proteins and aggregate-prone proteins. Due to its functionality to clear cytosolic contents, this highly conserved process has been shown to be a promising approach for treatment of diseases characterized by the formation of intracellular aggregates, such as aging of the brain and neurodegeneration.

Dysfunction in the autophagy-lysosome pathway (ALP) has been directly linked to neurodegenerative disorders. Recently, the transcription factor EB (TFEB) has been identified in Settembre, C., et. al., *TFEB links autophagy to lysosomal biogenesis*. Science, 2011. 332(6036): 1429-33, and Sardiello, M., et al., *A gene network regulating lysosomal biogenesis and function*. Science, 2009. 325(5939): 473-7, as a master regulator of ALP. TFEB transgene to increase TFEB expression, or small molecules aimed to stimulate nuclear translocation of endogenous TFEB promotes the clearance of toxic protein aggregates, thus providing a disease-modifying intervention for neurodegenerative disorders such as Parkinson's disease (PD), Alzheimer's disease (AD) and Huntington's disease (HD).

Current MTOR inhibitors, such as rapamycin and torin1, activate TFEB by promoting TFEB nuclear translocation. However, their pharmacokinetic profile and side effects make them less likely to be useful for long-term use in patients with neurodegenerative diseases. Disaccharides, such as trehalose and sucrose, activate TFEB in an MTOR-independent manner and may be beneficial for neurodegenerative diseases. However, the blood-brain barrier (BBB) permeability of trehalose and sucrose is poor. Discovery of small molecules which directly target TFEB hold great promise for the development of efficient neuroprotective therapies.

It is an objective of the current invention to provide for a small molecule compound having good BBB permeability and potent TFEB-activating effects for the treatment of neurodegenerative diseases. The present invention provides a compound having simple chemical structure which can be easily synthesized in large scale. The present invention provides a compound that directly binds to and activates TFEB without inhibiting MTOR pathway, thus eliminating possible MTOR-associated complications. A further objective of the current invention is to provide a method for treating lysosomal storage disorders and diseases that can benefit from autophagy, including but not limited to neurodegenerative disorders, immunological diseases, cardiac diseases and cancer.

SUMMARY OF THE INVENTION

The present invention relates to a composition comprising an autophagy enhancement compound. In particular, the present invention relates to a composition comprising a small molecule being able to enhance autophagy and lysosome biogenesis by activating the gene TFEB which can prevent the accumulation of toxic protein aggregates in treating neurodegenerative diseases such as Parkinson's, Alzheimer's and Huntington's diseases.

The present invention discloses a potent activator of TFEB that enhances autophagy and lysosome biogenesis in neuronal and non-neuronal cells. In comparison to currently known TFEB activators, the advantages of the present invention are: 1) The compound of the present invention is a small lipid molecule with good BBB permeability and potent TFEB-activating property; 2) The chemical structure of the compound of the present invention is simple and it can be easily synthesized in large scale for pre-clinical and clinical studies; 3) Compound of the present invention activates TFEB without inhibiting MTOR pathway, thus eliminating possible MTOR-associated complications in clinical trials. Therefore, the present invention has a wide field of application in the treatment of lysosomal storage disorders and common neurodegenerative diseases.

In a first aspect of the present invention, there is provided three potent autophagy enhancers. The three compounds (namely A2, B3 and C1) induce autophagy in neuronal-like N2a cells. The three compounds are synthesized mono-carbonyl analogs of curcumin and their chemical names are:

A2: 1,5-bis(3-(trifluoromethyl)phenyl)penta-1,4-dien-3-one

B3: 1,5-bis(4-hydroxyphenyl)penta-1,4-dien-3-one

C1: 1,5-bis(2-methoxyphenyl)penta-1,4-dien-3-one

In another embodiment of the present invention, it is provided that the three compounds A2, B3 and C1 promote the degradation of wild-type and A53T mutant alpha-synuclein (SNCA) in cell culture.

In a further embodiment of the present invention, there is provided that compounds A2 and B3 induce autophagy through inhibiting AKT/MTOR pathway.

In yet a further embodiment of the present invention, there is provided that compound C1 activates transcription factor EB (TFEB), an essential regulator of autophagy and lysosome biogenesis. C1 significantly increases endogenous TFEB expression and promotes the nuclear translocation of TFEB.

It is known that MTOR pathway is a key regulator of cell growth and proliferation. In another embodiment of the present invention there is provided that compound C1 activates TFEB-mediated autophagy without inhibiting MTOR pathway.

In yet a further embodiment of the present invention, there is provided that C1 directly binds to TFEB and inhibits MTOR-TFEB-YWHA interaction, which releases TFEB from MTOR complex and promotes TFEB nuclear translocation.

In yet another embodiment of the present invention, there is provided that compound C1 enhances TFEB-mediated autophagy and lysosome biogenesis in non-neuronal cells and neuronal cells.

In yet another embodiment of the present invention, there is provided that the medium lethal dose ($LD_{50}$) value of C1 is 175 mg/kg in rats by single-dose intravenous (IV) tail vein injection.

In yet another embodiment of the present invention, there is provided that the average concentration of C1 in brain tissues is 0.26±0.063 µg/g and 0.849±0.302 µg/g after 6 h short-term and chronic oral administration of C1 (10 mg/kg) in rats respectively.

In yet another embodiment of the present invention there is provided that short-term oral administration of curcumin analog C1 activates TFEB and autophagy in rats brains, and chronic administration of C1 promotes the degradation of endogenous SNCA in rats brains.

A second aspect of the present invention provides a method for treating neurodegenerative disorders without obvious side effects caused by mTOR inhibition comprising administering a composition comprising compound C1. Such neurodegenerative diseases comprise but are not limited to the following: Alzheimer's disease, Parkinson's disease, Huntington's disease, Creutzfeldt-Jakob disease.

In an embodiment of the second aspect of the present invention, C1 is administered at 1.62 mg/kg to 28.38 mg/kg per body weight of the subject in need thereof.

In another embodiment of the second aspect of the present invention, the composition is administered via oral administration and/or intravenous injection.

A third aspect of the present invention provides a method for enhancing autophagy in cells comprising providing a mono-carbonyl analog of curcumin having a formula of

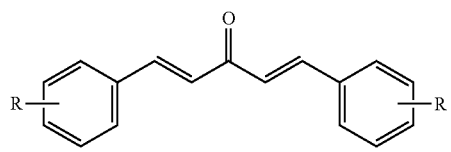

wherein R is independently selected from $CF_3$, OH or $OCH_3$.

In a first embodiment of the third aspect of the present invention, the mono-carbonyl analog of curcumin having the formula of A2:

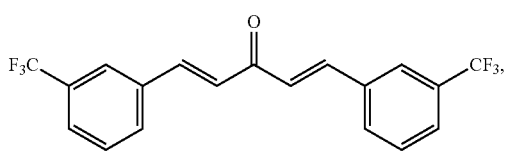

1,5-bis(3-(trifluoromethyl)phenyl)penta-1,4-dien-3-one.

In a second embodiment of the third aspect of the present invention, the mono-carbonyl analog of curcumin having the formula of B3:

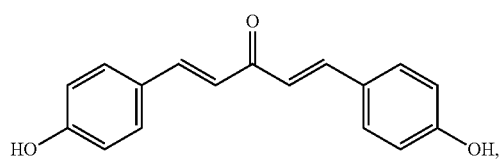

1,5-bis(4-hydroxyphenyl)penta-1,4-dien-3-one.

In a third embodiment of the third aspect of the present invention, the mono-carbonyl analog of curcumin having the formula of C1:

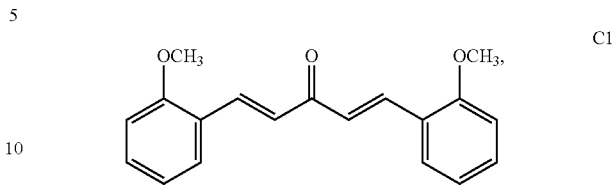

1,5-bis(2-methoxyphenyl)penta-1,4-dien-3-one.

In a fourth aspect of the present invention, there is provided a method for enhancing lysosome biogenesis in cells comprising providing a mono-carbonyl analogs of curcumin having a formula of

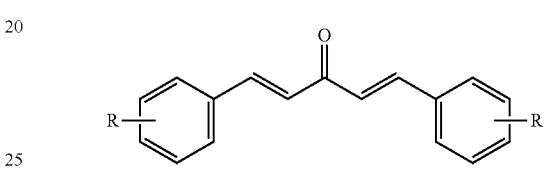

wherein R is OCH3.

In a first embodiment of the forth aspect of the present invention the mono-carbonyl analog of curcumin having a formula of C1:

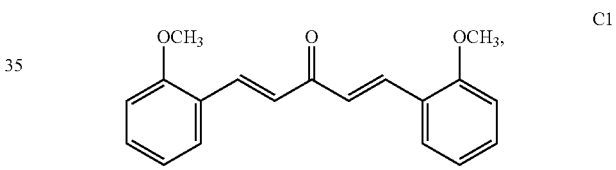

1,5-bis(2-methoxyphenyl)penta-1,4-dien-3-one.

In a second embodiment of the fourth aspect of the present invention, the mono-carbonyl analog binds to and activates TFEB in cells.

In the third and fourth aspects of the present invention, the cells are non-neuronal cells or neuronal cells.

Throughout the present specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the present invention.

Furthermore, throughout the present specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the present invention and apply throughout. Unless otherwise defined, all other technical terms used herein have the same meaning as commonly understood to one of ordinary skill in the art to which the invention belongs.

Other aspects and advantages of the present invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which:

FIG. 3 shows the effects of curcumin analogs on mTOR pathway. N2a cells were treated with curcumin (Cur, 10 ìM), A2, B3 and C1 (1 ìM) for 12 h. Torin 1 (1 ìM) treatment for 2 h was used as a positive control. FIG. 3A is a representative blots shows the expression of phosphorylated (p–) and total RPS6KB1/P70S6K, MTOR and AKT. FIG. 3B is a bar chart showing the expression of phosphorylated (p–) and total RPS6KB1/P70S6K, MTOR and AKT. Data are presented as the mean±SD from three independent experiments. *p<0.05 vs. the control (0.1% DMSO).

FIG. 4 shows effects of curcumin and analogs A2, B3 and C1 activate the expression of endogenous TFEB in N2a cells. Cells were treated with curcumin (Cur, 10 µM), A2, B3 and C1 (1 µM) for 12 h. FIG. 4A shows fluorescence images (at 50 and 10 µm scale) of cells fixed and stained with TFEB antibody and DAPI. FIG. 4B shows TFEB intensity per cell. Data is quantified by ImageJ software and is presented as mean±SD of three replicates for each treatment conditions. At least 1000 cells are analyzed in each treatment group. *p<0.05 vs. the control (0.1% DMSO). FIG. 4C is a western blot showing the expression of endogenous TFEB. FIG. 4D shows the relative intensity of TFEB normalized to that of ACTB/β-actin. Data are presented as the mean±SD from three independent experiments. *p<0.05 vs. the control (0.1% DMSO). FIG. 4E is fluorescence images showing expression of 3× Flag-TFEB in Hela cells having treated with Cur (10 µM), A2, B3 and C1 (1 µM) for 12 h. Torin 1 (1 µM) treatment for 2 h is used as a positive control. Cells were fixed and stained with anti-Flag antibody. FIG. 4F shows percentage of cells with nuclear staining of TFEB; nuclear staining of TFEB is quantified by counting of the fluorescent cells in three random fields of view. FIG. 4G is the western blot showing the expression of Flag-tagged TFEB in the cytosolic (Cyt.) and nuclear (Nuc.) fractions. ACTB and H3F3A (H3 histone, family 3A) are used as loading control of cytoplasmic and nuclear fraction, respectively. FIG. 4H is showing the relative intensity of TFEB in the cytosolic and nuclear fractions. Data are presented as the mean±SD from three independent experiments. *p<0.05 vs. the control (0.1% DMSO).

FIG. 5 shows C1 inhibits MTOR-TFEB-YWHA interaction. Hela cells stably expressing 3× Flag-TFEB are treated with C1 (1 µM) for 12 h. Endogenous MTOR and YWHA are co-immunoprecipitated with Flag-TFEB. Western blots and levels of immunoprecipitated MTOR (FIG. 5A) and YWHA (FIG. 5B) normalized to their corresponding levels in whole cell lysates (WCL). Data are presented as the mean±SD from three independent experiments. *p<0.05 vs. the control. WB— western blot and IP— immunoprecipitation

FIG. 9 shows short-term administration of C1 increases the expression of TFEB and enhances autophagy in rat brain. SD rats (n=6 per group) are orally administered by gavage with C1 (10 mg/kg and 25 mg/kg per day) or vehicle (1% CMC-Na) for 24 h. An additional dosage of C1 was given for 6 h before the rats were killed.

FIG. 10 shows effects of short-term administration of C1 on MTOR pathway, TFEB nuclear translocation and MTOR-TFEB interaction. SD rats (n=6 per group) are orally administered by gavage with C1 (10 mg/kg and 25 mg/kg per day) or vehicle (1% CMC-Na) for 24 h. An additional dosage of C1 is given for 6 h before the rats are killed. FIG. 10A shows western blot (left) and quantitative data (right) of MTOR and RPS6KB1 expressions having treated with C1 on MTOR pathway in the frontal cortex. Data are presented as the mean±SD (n=6). FIG. 10B is western blot (left) and quantitative data (right) showing TFEB nuclear translocation after C1 treatment (n=4). FIG. 10C shows immunoprecipitation data of MTOR-TFEB interaction after C1 treatment in the frontal cortex (n=4). *p<0.05 vs. the vehicle treatment.

FIG. 11 shows chronic administration of C1 enhances autophagy and promotes the degradation of endogenous SNCA in rat brain. SD rats (n=6 per group) are orally administered by gavage with C1 (10 mg/kg per day) or vehicle (1% CMC-Na) for 21 days. An additional dosage of C1 is given for 6 h before the rats are killed.

DETAILED DESCRIPTION OF THE INVENTION

Figures 1, 1A:
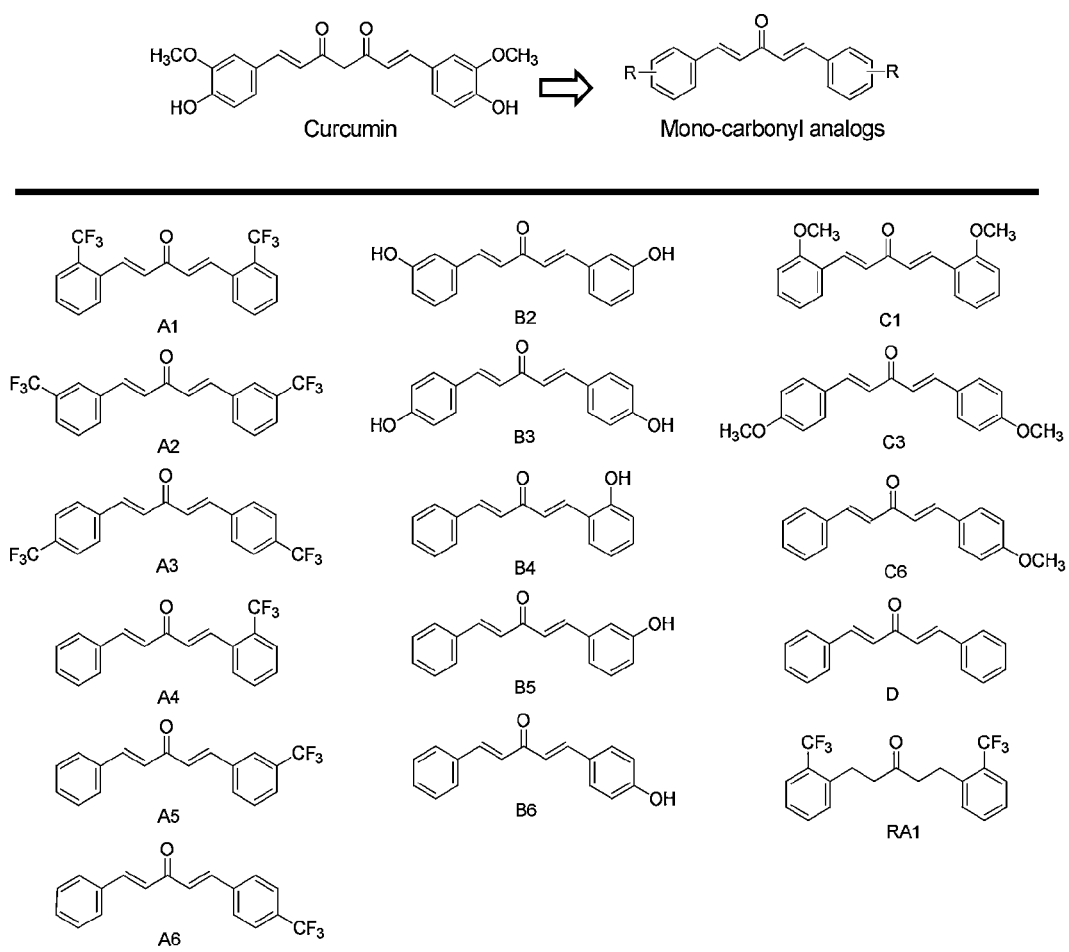
FIG. 1 shows the chemical structure of mono-carbonyl analogs of curcumin (FIG. 1A) and cytotoxicity of mono-carbonyl analogs of curcumin (FIG. 1B). Data are presented as the mean±SD from three independent experiments. *p<0.05 vs. the control (0.1% DMSO).

The present invention is not to be limited in scope by any of the specific embodiments described herein. The following embodiments are presented for exemplification only.

DEFINITIONS

"a," "an," and "the" as used herein include "at least one" and "one or more" unless stated otherwise. Thus, for example, reference to "a pharmacologically acceptable carrier" includes mixtures of two or more carriers as well as a single carrier, and the like.

The term "autophagy" refers to macroautophagy, unless stated otherwise, is the catabolic process involving the degradation of a cell's own components; such as, long lived proteins, protein aggregates, cellular organelles, cell membranes, organelle membranes, and other cellular components. The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. The term autophagy may also refer to one of the mechanisms by which a starving cell re-allocates nutrients from unnecessary processes to more essential processes. Also, for example, autophagy may inhibit the progression of some diseases and play a protective role against infection by intracellular pathogens.

The diseases that benefit from autophagy inducement are diseases of which conditions are ameliorated, reduced or eliminated by autophagy and can be treated by the inventions as disclosed herein. The diseases include aggregate-prone disorder which represents any disease, disorder or condition associated with or caused by abnormal protein aggregates that are not sufficiently destroyed by a natural autophagy process in an organism and can be treated through degradation thereof via induction of autophagy by the subject invention. For example, such diseases include Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, x-linked spinobulbar muscular atrophy, and neuronal intranuclear hyaline inclusion disease. The diseases also include cancer e.g., any cancer wherein the induction of autophagy would inhibit cell growth and division, reduce mutagenesis, remove mitochondria and other organelles damaged by reactive oxygen species or kill developing tumor cells. They can be chronic diseases which refers to persistent and lasting diseases, medical conditions or diseases that have developed slowly. The diseases that can be treated by the subject invention also include, but not limited to, cardiovascular disorders, autoimmune disorders, metabolic disorders, hamartoma syndrome, genetic muscle disorders, and myopathies.

The present invention provides a small molecule being able to enhance autophagy and lysosome biogenesis by activating TFEB. The molecule is a mono-carbonyl analog of curcumin. The molecule directly binds to TFEB, promote its expression and nuclear translocation. The molecule can prevent the accumulation of toxic protein aggregates in treating neurodegenerative diseases such as Parkinson's, Alzheimer's and Huntington's diseases. The molecule activates TFEB without inhibiting MTOR pathway, which is a key regulator of cell growth and proliferation.

TFEB has been identified as a master gene regulating lysosome biogenesis and autophagy. Pharmacological activation of TFEB promotes cellular clearance of accumulated toxic molecules. The present invention discloses a potent activator of TFEB that enhances autophagy and lysosome biogenesis in neuronal and non-neuronal cells. In comparison to currently known TFEB activators, the advantages of the present invention are: 1) compound of the present invention is a small lipid molecule with good BBB permeability and potent TFEB-activating effects for treating neurodegenerative diseases; 2) chemical structure of compound of the present invention is simple and it can be easily synthesized in large scale for pre-clinical and clinical studies; 3) compound of the present invention activates TFEB without inhibiting MTOR pathway, thus eliminating possible MTOR-associated complications in clinical trials. Therefore, the present invention has a wide field of application in the treatment of lysosomal storage disorders and common neurodegenerative diseases.

The present invention provides a method for enhancing autophagy in cells comprising providing a mono-carbonyl analog of curcumin having a formula of Formula I

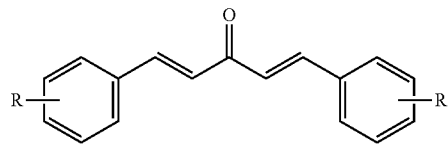

wherein R are independently selected from $CF_3$, OH and $OCH_3$.

In a first embodiment of the present invention, the mono-carbonyl analog of curcumin having a formula of A2:

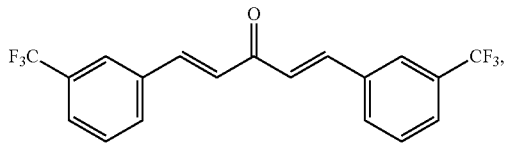

1,5-bis(3-(trifluoromethyl)phenyl)penta-1,4-dien-3-one.

In a second embodiment of the present invention, the mono-carbonyl analog of curcumin having a formula of B3:

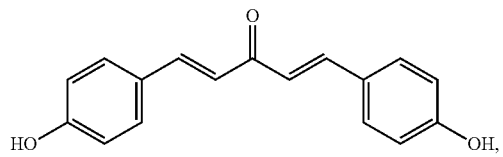

1,5-bis(4-hydroxyphenyl)penta-1,4-dien-3-one.

In a third embodiment of the present invention, the mono-carbonyl analog of curcumin having a formula of C1:

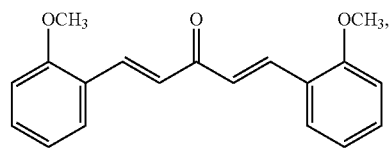

1,5-bis(2-methoxyphenyl)penta-1,4-dien-3-one.

In a second aspect of the present invention there is provided a method for enhancing lysosome biogenesis in cells comprising providing a mono-carbonyl analog of curcumin having a formula of

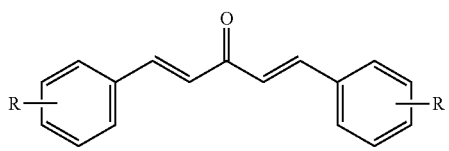

wherein R is OCH3.

In a first embodiment of the second aspect of the present invention there is provided a method for enhancing lysosome biogenesis in cells comprising providing a mono-carbonyl analog of curcumin having a formula of C1:

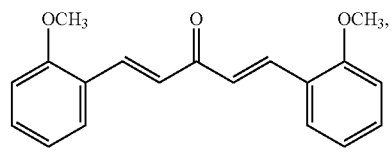

1,5-bis(2-methoxyphenyl)penta-1,4-dien-3-one.

In a second embodiment of the second aspect of the present invention, the mono-carbonyl analog binds to and activates TFEB in cells.

In yet another embodiment of the present invention, the cells are non-neuronal cells or neuronal cells.

In a third aspect of the present invention there is provided a method of treating neurodegenerative diseases by administering a composition comprising a mono-carbonyl analog of Formula I to a subject in need thereof, wherein R is independently selected from CF3, OH and OCH3.

In a first embodiment of the third aspect of the present invention, the neurodegenerative diseases comprising Alzheimer's disease, Parkinson's disease, Huntington's disease and Creutzfeldt-Jakob disease.

In a second embodiment of the third aspect of the present invention, the composition comprises 1.62 mg/kg to 28.38 mg/kg of C1.

In a third embodiment of the third aspect of the present invention, the composition is administered via oral administration, intravenous injection or both.

The embodiments of the present invention are further illustrated by the following working examples, which should not be construed as further limiting.

EXAMPLES

In the following examples, the following materials are used; various commercial sources for the materials are provided. Details of the various protocols are also set forth below:

Reagents and Antibodies.

The trial samples of mono-carbonyl analogs of curcumin are kindly provided by Dr. Zhou Bo (Lanzhou University, China). Compound C1 ((1E,4E)-1,5-bis(2-methoxy-phenyl)penta-1,4-dien-3-one) is synthesized from 2-methoxybenzaldehyde in an one-step reaction. The structure and purity of the compound are confirmed by 1H NMR and HPLC. Curcumin (08511), chloroquine (C6628), doxycycline (D9891), Anti-Flag M2 (F1804) are purchased from Sigma-Aldrich. Torin 1 (2273-5) is purchased from BioVision Inc. Anti-phospho-AKT (ser473) (9271), anti-AKT (9272), anti-phospho-MTOR (Ser2448) (2971), anti-MTOR (2983), anti-phospho-P70S6K/RPS6KB1 (Thr389) (9234) and anti-P70S6K/RPS6KB1 (9202), pan-14-3-3/YWHA (8312) antibodies are purchased from Cell Signaling Technology. Anti-á-syn/SNCA antibody (610786) is purchased from BD Transduction Laboratories. HRP-conjugated goat anti-mouse (115-035-003) and goat anti-rabbit (111-035-003) secondary antibodies are purchased from Jackson ImmunoResearch. Anti-ⓐ-actin/ACTB (sc-47778) is purchased from Santa Cruz Biotechnology. Anti-ATG5 (NB110-53818) and anti-LC3 (NB100-2220) antibodies were purchased from Novus Biologicals. Anti-TFEB (13372-1-AP) was purchased from Proteintech. Mouse Atg5 siRNA (L-064838-00-0005) and non-target siRNA, human TFEB siRNA (M-009798-02-0005) and non-target siRNA are purchased from Dharmacon. DMEM (11965-126), FBS (10270-106), Opti-MEM I (31985-070), horse serum (16050-122), Hygromycin B (10687-010), G418 (10131-035), Alexa Fluor®488 goat anti-mouse IgG (A-11001) and Alexa Fluor®594 goat anti-rabbit IgG (A-11012) are purchased from Life Technologies.

Cell Culture and Drug Treatment.

N2a, Hela and Hela cells stably expressing 3×-Flag-TFEB are cultured in DMEM supplemented with 10% FBS. SH-SY5Y cells are cultured in DMEM/F12 supplemented with 10% FBS. For drug treatment, the full medium is replaced by fresh Opti-MEM I and then the compounds (in 0.1% DMSO) are added to the cells and incubated for 12 h. Inducible PC12 cells overexpressing SNCA (WT and A53T) (a kind gift from Prof. David C. Rubinsztein at Cambridge University) are grown in DMEM supplemented with 10% horse serum, 5% FBS, 50 µg/ml G418, and 150 µg/ml hygromycin B at 37° C., 10% CO2. Cells are treated with 2 µg/ml doxycycline (Dox) for 24 h to induce SNCA expression. The full medium is changed to Opti-MEM I containing the testing compounds for another 48 h.

LDH Assay.

The cytotoxicity is determined by measurement of LDH release from damaged cells using LDH Kit (11644793001, Roche) according to the manufacturer's protocol.

siRNA Knock-Down.

Mouse Atg5 siRNA (25 nM) or human TFEB (100 nM) siRNA and the non-target siRNAs are transfected with Lipofectamine RNAiMAX (13778030, Invitrogen) and incubated at 37° C. for 72 h.

Animals and Treatments.

All animal care and procedures are approved by the Hong Kong Baptist University Committee on the Use of Human and Animal Subjects in Teaching and Research. Adult male Sprague-Dawley (SD) rats weighted 350-400 g are maintained on ad libitum food and water with a 12-hour light/dark cycle in a controlled environment. For short-term treatment, rats (n=6 per group) are orally administered by gavage with C1 (10 mg/kg and 25 mg/kg per day) or vehicle (1% sodium carbonyl methylcellulose (CMC-Na)) for 24 h. For chronic treatment, C1 (10 mg/kg per day) is given by gavage to rats for 21 days. At the end of each treatment, an additional dosage of C1 is given for 6 h before the rats are killed. Livers and major brain regions dissected are snap-frozen in liquid nitrogen.

Quantitative Real-Time PCR.

Total RNA is extracted from cells and tissues using RNeasy Plus Mini Kit (74134, Qiagen). Reverse transcription is performed using High-Capacity cDNA Reverse Transcription Kit (4368814, Life Technologies). Autophagy and lysosome gene primers are synthesized by Life Technologies and the oligonucleotide sequences are listed in Table 1. Real-time PCR is carried out with the Fast SYBRR Green Master Mix (4385612, Life Technologies) using the ViiA™ 7 Real-Time PCR System (Life Technologies). Fold changes are calculated using the ΔΔCT method and the results were normalized against an internal control (GAPDH or ACTS).

TABLE 1

Primer sequences used in real-time PCR analysis.

| SEQ ID No. | Gene name | Forward primer | SEQ ID No. | Reverse primer |
|---|---|---|---|---|
| Human primers | | | | |
| 1 | ATG9B | ACCCTGTCAGATGCCATCCTAC | 2 | CCAGTAGCTGAAGAGGTTGCAG |
| 3 | ATG10 | GGTGATAGTTGGGAATGGAGACC | 4 | GTCTGTCCATGGGTAGATGCTC |
| 5 | ATG16L1 | CTACGGAAGAGAACCAGGAGCT | 6 | CTGGTAGAGGTTCCTTTGCTGC |
| 7 | BCL2 | ATCGCCCTGTGGATGACTGAGT | 8 | GCCAGGAGAAATCAAACAGAGGC |
| 9 | CLN3 | GAACACTTCCCTGAGTCACGCT | 10 | AGGTGAAACGGATGCGACAGCA |
| 11 | GABARAPL1 | TTGTAGAGAAGGCTCCAAAAGCC | 12 | GGTCTCAGGTGGATTCTCTTCC |
| 13 | GABARAPL2 | CCAGCTTCCTTCTGAAAAGGCG | 14 | TTCTCTCCGCTGTAGGCCACAT |
| 15 | MAP1LC3B | GAGAAGCAGCTTCCTGTTCTGG | 16 | GTGTCCGTTCACCAACAGGAAG |
| 17 | MAPK14 | GAGCGTTACCAGAACCTGTCTC | 18 | AGTAACCGCAGTTCTCTGTAGGT |
| 19 | SQSTM1 | TGTGTAGCGTCTGCGAGGGAAA | 20 | AGTGTCCGTGTTTCACCTTCCG |
| 21 | VPS11 | GCTATACCAAGCTCAAGGACAGC | 22 | ATGGTTCTCCGCCAGATACAGG |
| 23 | VPS18 | ACTTGGGCAAGGCAAATGAGCC | 24 | CCTTCTGTCCATTTCGGTTCACG |
| 25 | WIPI1 | CTTCAAGCTGGAACAGGTCACC | 26 | CGGAGAAGTTCAAGCGTGCAGT |
| 27 | CLCN7 | CACAGTTGCCTTCGTGCTGATC | 28 | TGGAGTTGTACTCGCCATCTGC |
| 29 | ATP6V0E1 | GGTGACCTGTTCAGTTTGCTGC | 30 | GAGCATGTCTTCTTCCTCAAGGC |
| 31 | ATP6V1H | CGGGTCAATGAGTACCGCTTTG | 32 | GATACTGGAGCTGAAAGCCACAC |
| 33 | CTSA | GCTTCGTGAAGGAGTTCTCCCA | 34 | CTGTGGTCATCAGTATGGCTGC |
| 35 | CTSB | GCTTCGATGCACGGGAACAATG | 36 | CATTGGTGTGGATGCAGATCCG |
| 37 | CTSD | GCAAACTGCTGGACATCGCTTG | 38 | GCCATAGTGGATGTCAAACGAGG |
| 39 | CTSS | TGGATCACCACTGGCATCTCTG | 40 | GCTCCAGGTTGTGAAGCATCAC |
| 41 | GALNS | AGCAGACCACGTTTGAAGGAGG | 42 | GTGGTGAAGAGGTCCATGATGC |
| 43 | GBA | TGCTGCTCTCAACATCCTTGCC | 44 | TAGGTGCGGATGGAGAAGTCAC |
| 45 | GLA | GCAACCTTGACTGCCAGGAAGA | 46 | CTCATAACCTGCATCCTTCCAGC |

TABLE 1-continued

Primer sequences used in real-time PCR analysis.

| SEQ ID No. | Gene name | Forward primer | SEQ ID No. | Reverse primer |
|---|---|---|---|---|
| 47 | GNS | TCCACTGTTGGTTCGAGGACCT | 48 | TAGGTCGTAGCCAGCAATGTCC |
| 49 | HEXA | GGAGGTCATTGAATACGCACGG | 50 | GGATTCACTGGTCCAAAGGTGC |
| 51 | LAMP1 | CGTGTCACGAAGGCGTTTTCAG | 52 | CTGTTCTCGTCCAGCAGACACT |
| 53 | MCOLN1 | CGGACTGCTATACCTTCAGCGT | 54 | GGTGCTTACACTCCTGGATGTG |
| 55 | PSAP | GCCTCCAAGAATGTCATCCCTG | 56 | CAATCAGCTTGGTCACCTCCTTC |
| 57 | SCPEP1 | CATTCAGCGAGGGACCATCAAG | 58 | CCTCTGCCAGACCTTTGTCTTC |
| 59 | SGSH | AATGCCTTCACCTCGGTCAGCA | 60 | TGTCGAAGGAGTTGAAGTGGTGC |
| 61 | TFEB | CCTGGAGATGACCAACAAGCAG | 62 | TAGGCAGCTCCTGCTTCACCAC |
| 63 | TPP1 | GGTGGCTTCAGCAATGTGTTCC | 64 | GAAGTAACTGGATGGTGGCAGG |
| 65 | TMEM55B | CAGAGTTCACAGACCGCACTTTG | 66 | GGCAGTGACTGCCAAAAGCAAG |
| 67 | GAPDH | GTCTCCTCTGACTTCAACAGCG | 68 | ACCACCCTGTTGCTGTAGCCAA |
| Rat primers | | | | |
| 69 | Map1lc3a | AACAGGAGAAGGATGAAGACGG | 70 | TTGACTCAGAAGCCGAAGGTTT |
| 71 | Lamp1 | GCACCTCCAACTATTCCCTGAA | 72 | ACAGACCCAAACCTGTCACTTT |
| 73 | Tfeb | AATGGGAGCAACCGTACTTAGG | 74 | GAGGGAAGACAGGTCCATGAAG |
| 75 | Atp6v1h | CTCAGTATGTGCAGTGTGTTGC | 76 | TACAGTTCACCCCATCTGCTTC |
| 77 | Vps18 | GCTGATGATTCGCTCCATTGAC | 78 | AGTCTGGTAGCTGTATCCCTGT |
| 79 | Actb | CTGTGTGGATTGGTGGCTCTAT | 80 | GTAACAGTCCGCCTAGAAGCAT |

Western Blotting and Immunoprecipitation.

Cells are lysed on ice in 1× Lysis Buffer (9803, Life Technologies) with complete protease inhibitor mixture (04693124001, Roche Applied Science). Animal tissues are homogenized in nine volumes of ice-cold PBS supplemented with protease inhibitors. Cytosolic and nuclear fractions are isolated using protocols similar to those described previously. Anti-Flag or TFEB antibody is added to the whole cell lysates and Dynabeads® Protein G (10003D, Life Technologies) is used for immunoprecipitation. Proteins are separated by 10-15% SDS-PAGE, transferred, and blotted with the antibodies described. The blots are then incubated with secondary antibodies or the Clean-Blot IP Detection Reagent (21230, Thermo Scientific) at room temperature for 1 h. The protein signals are detected by ECL kit (32106, Pierce) and quantified using ImageJ software.

Immunocytochemistry.

Cells are seeded on coverslips placed in 24-well plates. After drug treatment, slices are fixed with 3.7% paraformaldehyde, permeabilised in 0.2% Triton X-100 and blocked with 5% BSA. After blocking, the slices are stained with anti-TFEB (1:200) or anti-Flag (1:500) antibodies overnight at 4° C. Alexa Fluor®488 (green) or Alexa Fluor®594 (red) secondary antibodies (1:500) are added for 1 h at room temperature. After nuclear staining with DAPI, the slices are mounted with FluorSave reagent (345789, Calbiochem). Cells are visualized using an Eclipse 80i fluorescence microscope (Nikon Instruments Inc.)

Statistical Analysis.

Each experiment is performed at least 3 times, and the results are presented as mean±SD. One-way analysis of variance (ANOVA) followed by the Student-Newman-Keuls test using the SigmaPlot 11.0 software packages. A probability value of $P<0.05$ is considered to be statistically significant.

Example I

New Autophagy Enhancers Identified from Monocarbonyl Analogs of Curcumin

Figures 1, 1B:
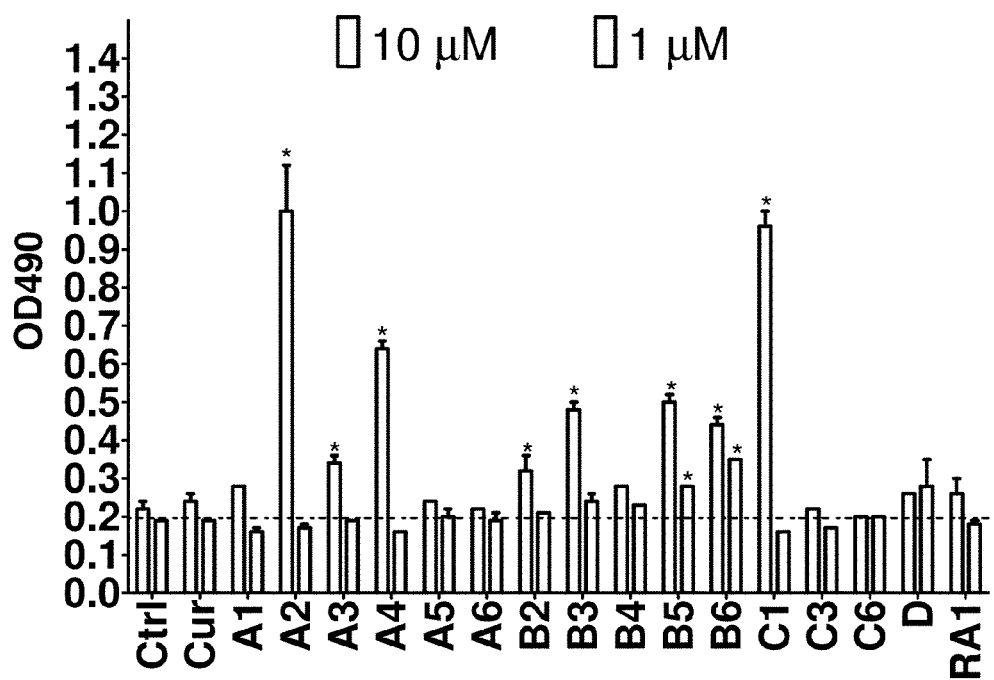
Figures 2, 2B:
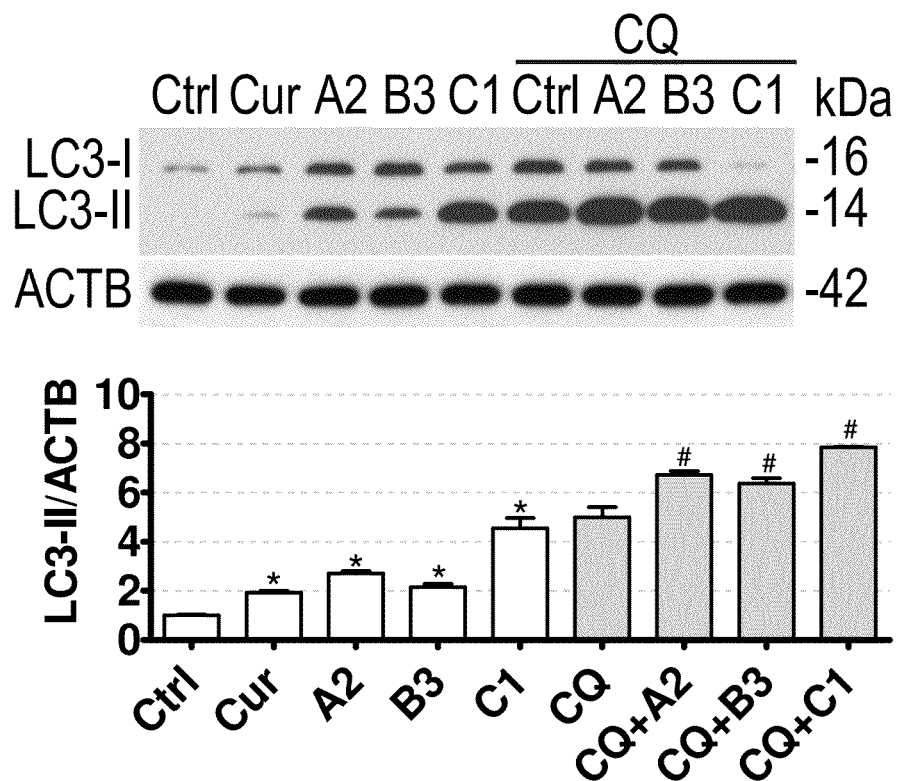
FIG. 2 shows western blots of LC3-II, an autophagy marker, and LC3-II relative intensity in N2a cells treated with curcumin analogs. N2a cells were treated with curcumin (Cur, 10 µM) and its analogs (1 µM) for 12 h (FIG. 2A). N2a cells were treated with Cur (10 µM), analogs A2, B3 and C1 (1 µM) with or without chloroquine (CQ, 20 µM) for 12 h (FIG. 2B). N2a cells were transfected with non-target siRNA (siNT) or Atg5 siRNA (siAtg5, 50 nM) for 72 h and then treated with Cur (10 µM) and analogs A2, B3 and C1 (1 µM) for 12 h (FIG. 2C). The expression of LC3-II is determined by western blot. Relative intensity is normalized to that of ACTB/β-actin. Data are presented as the mean±SD from three independent experiments. *p<0.05 vs. the control (0.1% DMSO); #p<0.05 vs. CQ treatment alone. N. S.=not significant.
Figures 2, 2C:
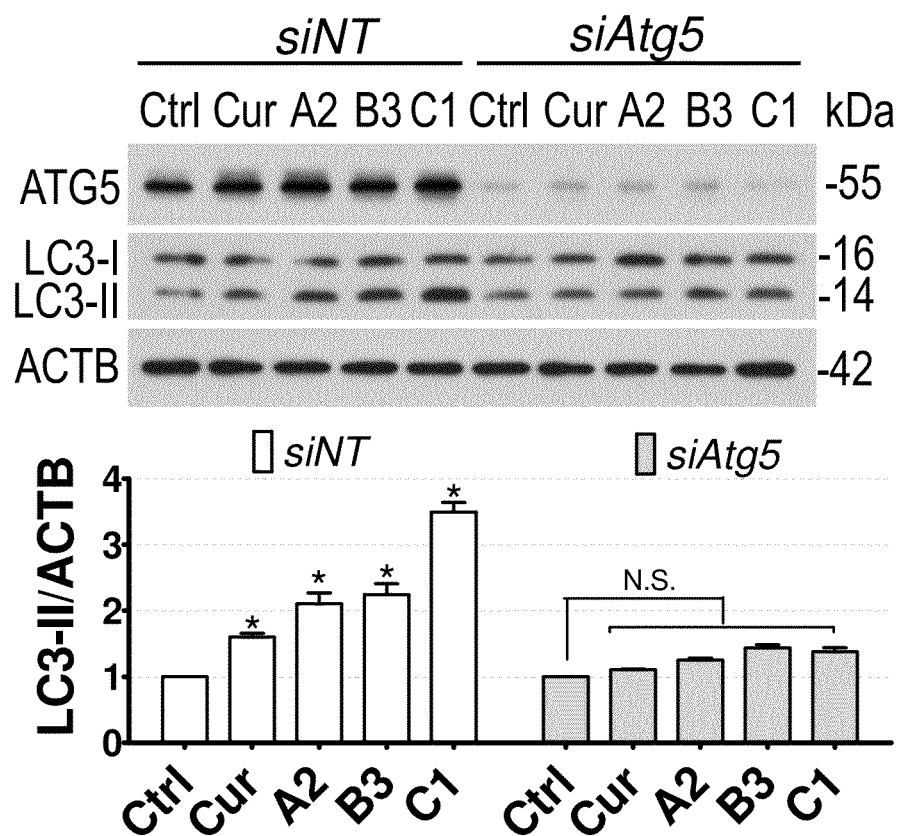

First, the inventors tested the cytotoxicity of the testing compounds at 1 µM and 10 µM for 24 h (as shown in FIG. 1A) by LDH assay (FIG. 1B) and used 1 µM concentration subsequently. Curcumin (10 µM) and analogs A2, B3 and C1 (1 µM) significantly increase the levels of microtubule-associated protein 1 light chain 3B (LC3B)-II in N2a cells compared to the vehicle control (0.1% DMSO) (FIG. 2A). In the presence of the lysosomal inhibitor chloroquine (CQ), these analogs further increase LC3-II levels compared with CQ treatment alone (FIG. 2B). Furthermore, in cells depletion of the autophagy-related gene 5 (Atg5) by siRNA, these compounds failed to increase the levels of LC3-II (FIG. 2C). The data indicate that curcumin analogs A2, B3 and C1 enhance autophagy rather than blocking lysosomal degradation.

Example II

Effects of Curcumin Analogs on MTOR Pathway

Since curcumin enhances autophagy through inhibiting MTOR pathway, the effects of the three newly identified autophagy enhancers on MTOR pathway of the present invention are confirmed. Similar to curcumin, A2 and B3 inhibit the phosphorylation of RPS6KB1/p70S6K, MTOR and AKT (FIG. 3A and FIG. 3B). Torin1, a potent MTOR inhibitor is used as a positive control. C1 significantly promotes the phosphorylation of RPS6KB1, MTOR and AKT (FIG. 3A and FIG. 3B).

Example III

Curcumin Analog C1 Activates TFEB in Cell Cultures

TFEB has been identified as a target of MTOR. Pharmacological inhibition of MTORC1 activates TFEB by promoting its nuclear translocation. However, the effects of curcumin and its analogs which inhibit MTOR pathway on TFEB has not been studied. Firstly, the expression and distribution of endogenous TFEB in N2a cells treated with curcumin and its analogs are determined. N2a cells are treated with curcumin (Cur, 10 µM), A2, B3 and C1 (1 µM) for 12 h. It is shown that compound C1 increases the total levels of TFEB and promotes its nuclear translocation (FIG. 4A-D). Curcumin, A2 and B3 show no effects on the expression or distribution of TFEB (FIG. 4A-D). Secondly, the effects of curcumin and its analogs on the distribution of TFEB in Hela cells stably expressing Flag-TFEB are determined by immunostaining and western blot. Similar to Torin 1 treatment, compound C1 significantly promotes the nuclear translocation of Flag-TFEB while curcumin, A2 and B3 show no effects (FIG. 4E-H). These data indicate that curcumin analog C1 represents a new activator of TFEB which affects both its expression and translocation.

Example IV

Curcumin Analog C1 Binds to TFEB and Inhibits MTOR-TFEB-YWHA Interaction

Figure 6:
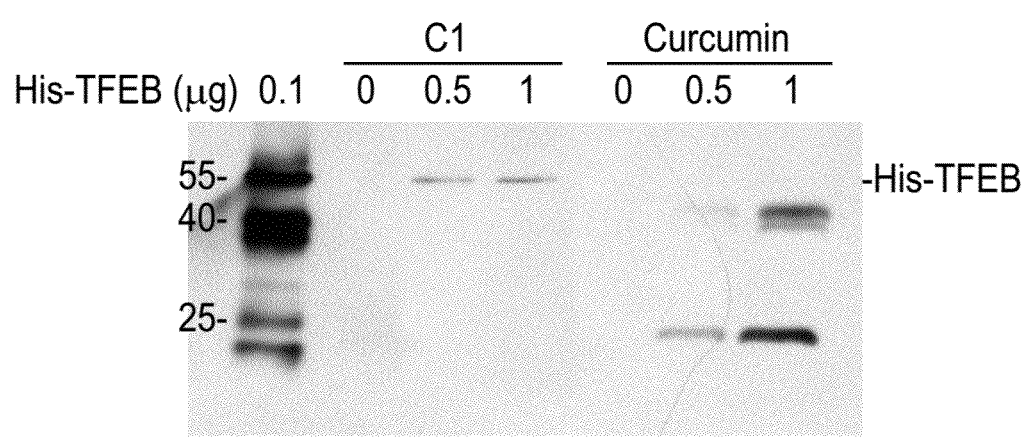
FIG. 6 shows western blot of binding of solid-phase C1 or curcumin with recombinant TFEB protein.

Hela cells stably expressing 3×Flag-TFEB are treated with C1 (1 µM) for 12 h. Endogenous MTOR (A) and YWHA (B) are co-immunoprecipitated with Flag-TFEB. The levels of immunoprecipitated MTOR and YWHA are normalized to their corresponding levels in whole cell lysates (WCL). In Hela cells stably expressing Flag-TFEB, C1 treatment does not affect the levels of endogenous MTOR (FIG. 5A) and YWHA (FIG. 5B). However, when MTOR and YWHA coimmunoprecipitated with Flag-TFEB after C1 treatment, interaction of MTOR and YWHA is decreased as compared with control. This indicates that C1 inhibits MTOR-TFEB-YWHA interaction. Furthermore, purified His-TFEB (TP760282, ORIGENE) is diluted in RIPA buffer and 17 µmol curcumin (6.3 mg) or C1 (5 mg) powder is added into TFEB solution and incubated for 2 hours at 4° C. with shaking. The supernatant is discarded after centrifuge. The pellet (compounds and the bound protein) is washes 4 times in RIPA buffer and the bound proteins are eluted by adding 2% SDS sampling buffer. The bound proteins are separated on 10% SDS-polyacrylamide gel and visualized by TFEB antibody (Proteintech). It is shown that C1, but not curcumin, can directly bind to purified TFEB (FIG. 6). As seen in FIG. 6, the 55 kDa band of TFEB is only observed in treatment with compound C1.

Example V

Figure 7A:
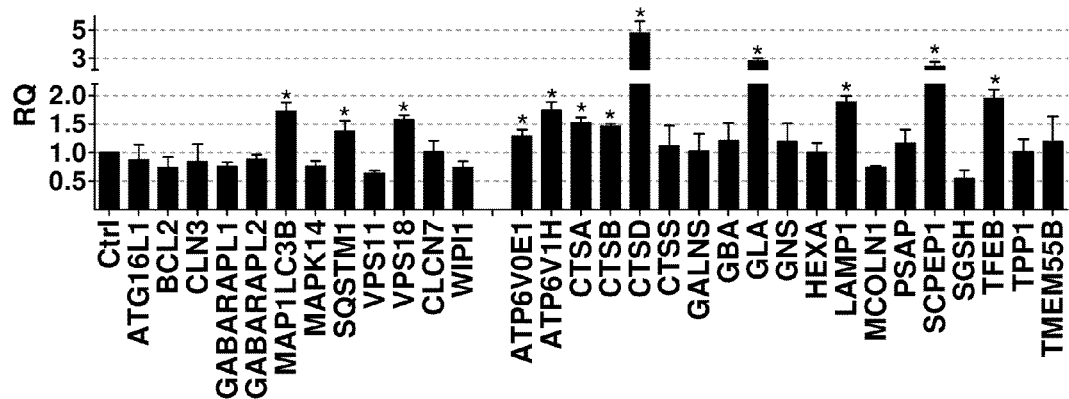
FIG. 7 shows curcumin analog C1 promotes TFEB-mediated autophagy and lysosomal biogenesis in cell cultures. Various gene expressions in Hela cells (FIG. 7A) and SH-SY5Y cells (FIG. 7B) after treated with C1 (1 µM) for 12 h. mRNA transcript abundance is assessed by real-time PCR using specific primers for the indicated genes. Relative quantification (RQ) is presented as means±SD of three independent experiments.
FIG. 7C is western blot showing the protein levels of autophagy marker (LC3-II), TFEB and lysosome markers (LAMP1, CTSD) in Hela and SH-SY5Y cells having treated with C1 (0.5, 1 µM) or sucrose (100 mM) for 12 h. The relative intensity of autophagy marker (LC3-II), TFEB and lysosome markers (LAMP1, CTSD) normalized to that of ACTB/β-actin in Hela cells (FIG. 7D) and SH-SY5Y cells (FIG. 7E). Data are presented as the mean±SD from three independent experiments. *p<0.05 vs. the control (0.1% DMSO).
FIG. 7F shows western blot (left) and bar chat (right) showing the expression of endogenous TFEB and LC3-II in Hela cells having transfected with non-target siRNA (siNT) or TFEB siRND (siTFEB, 100 nM) for 72 h and treated with C1 (1 µM) for 12 h. Autophagy-enhancing effect of C1 is TFEB-dependent. Data are presented as the mean±SD from three independent experiments. *p<0.05 vs. the control. N. S.=not significant.
Figure 7B:
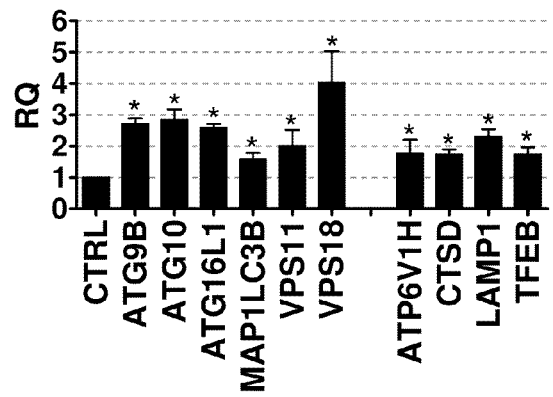
Figure 7C:
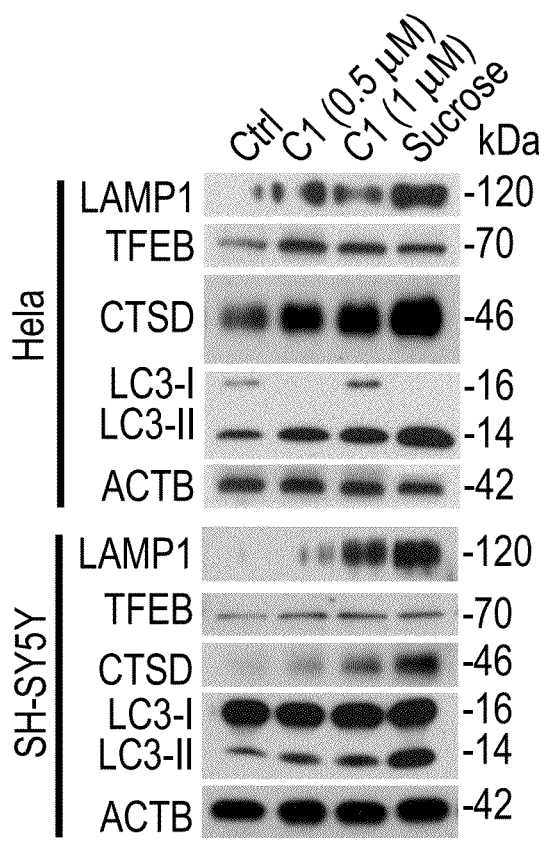
Figure 7D:
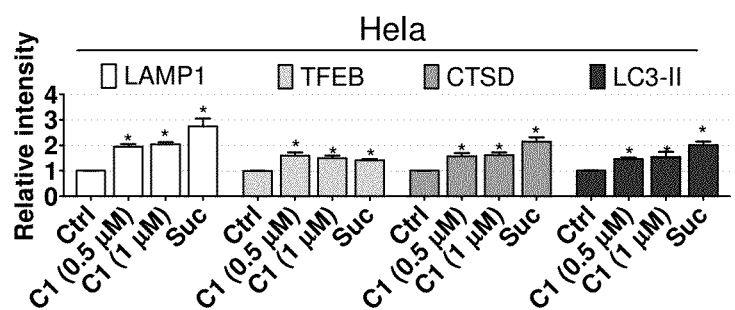
Figure 7E:
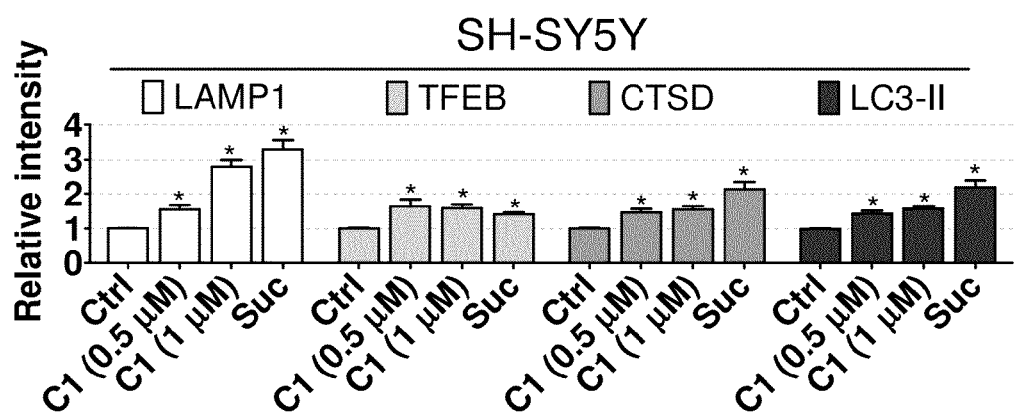
Figure 7F:
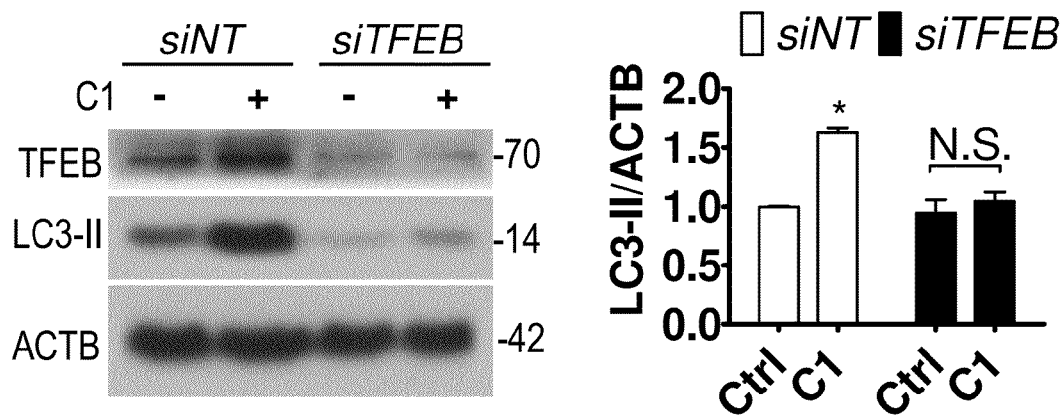

Curcumin Analog C1 Activates TFEB-Mediated Autophagy and Lysosomal Biogenesis in Cell Cultures In the non-neuronal Hela and neuronal SH-SY5Y cell lines, TFEB genes and a series of genes involved in autophagy and lysosome biogenesis are shown to be up-regulated by C1 treatment in Hela (FIG. 7A) and SH-SY5Y (FIG. 7B) cells. The changes in gene expression by C1 treatment are more sensitive in Hela cells than in SH-SY5Y cells. Next, the expression of TFEB, autophagy marker (LC3B) and lysosome markers (LAMP1 and CTSD) are determined by western blot (FIG. 7C). Sucrose, a TFEB activator is used as a positive control. As expected, C1 at different concentrations increased the protein levels of TFEB and activated autophagy/lysosomal biogenesis in Hela (FIG. 7D) and SH-SY5Y (FIG. 7E) cells. In Hela cells transfected with TFEB siRNA, the increase in LC3-II levels by C1 treatment is blocked, indicating that the autophagy-enhancing effect of C1 is TFEB-dependent (FIG. 7F).

Example VI

Curcumin Analog C1 Promotes the Degradation of SNCA

Figure 8:
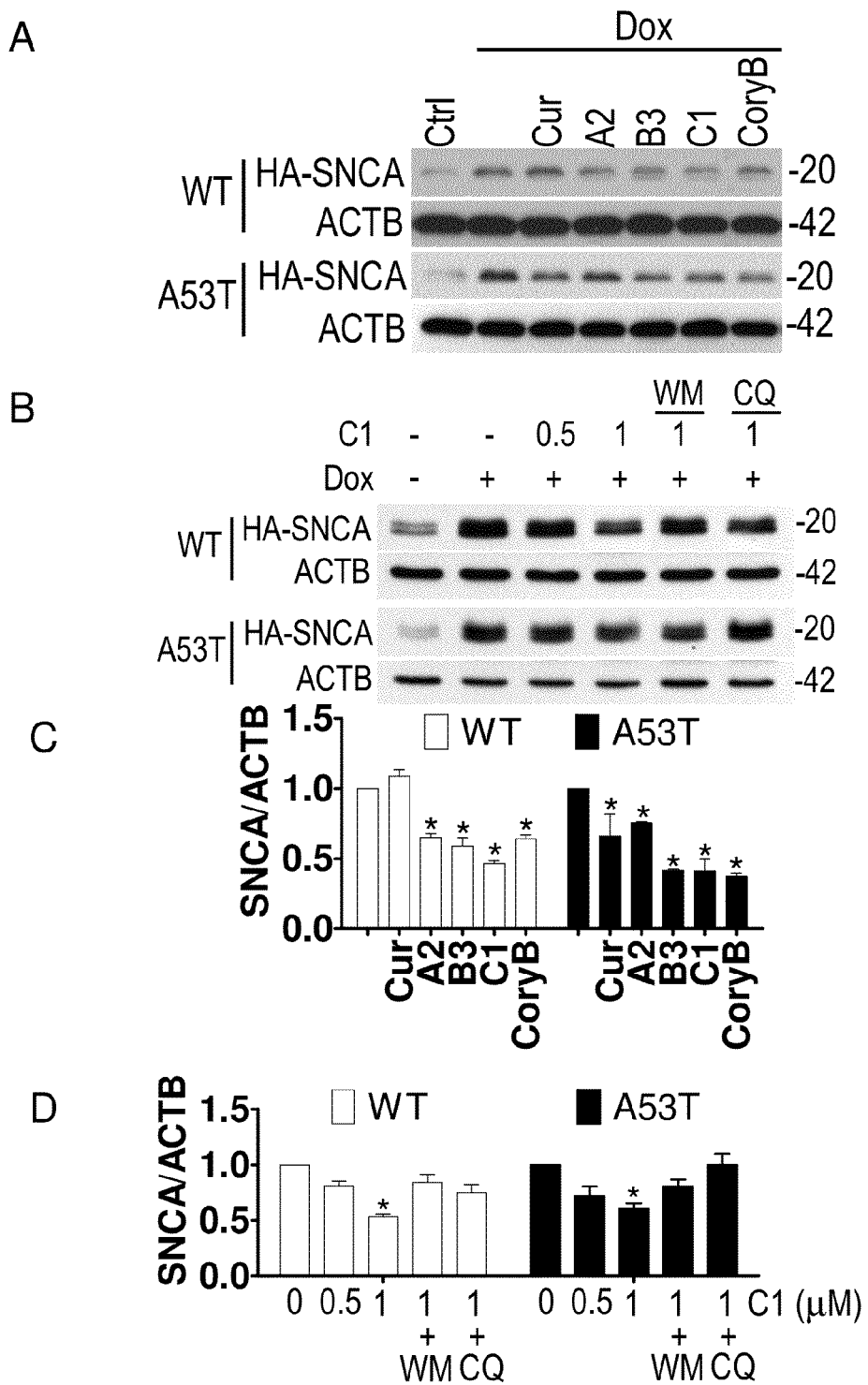
FIG. 8 shows curcumin analogs promotes the degradation of SNCA. Expression and intensity of HA-tagged wild-type (WT) or A53T mutant SNCA in inducible PC12 cells are treated with doxycycline (Dox, 2 µg/ml) for 24 h, and then treated with curcumin (10 µM), A2, B3 and C1 (1 µM) for another 48 h (A, C) in the presence or absence of chloroquine (CQ, 20 µM) and wortmannin (WM, 1 µM) (B, D). The expression of HA-SNCA is determined by western blots and quantified from three independent experiments. Corynoxine B (Cory B, 25 µM) is used as a positive control. Relative intensity is normalized to that of ACTB/β-actin. Data are presented as the mean±SD from three independent experiments. *p<0.05 vs. the control (0.1% DMSO).

Inducible PC12 cells are treated with doxycycline (Dox, 2 µg/ml) for 24 h to induce the expression of HA-tagged wild-type (WT) or A53T mutant SNCA, and then treated with curcumin (10 µM), A2, B3 and C1 (1 µM) for another 48 h (A, C) in the presence or absence of chloroquine (CQ, 20 µM) and wortmannin (WM, 1 µM) (B, D). The expression of HA-SNCA is determined by western blots and quantified from three independent experiments. Corynoxine B (Cory B, 25 µM) is used as a positive control. In inducible PC12 cells overexpressing $SNCA^{WT}$ or $SNCA^{A53T}$, it is found that curcumin (10 ìM) promotes the degradation of $SNCA^{A53T}$ but had no effect on $SNCA^{WT}$. However, curcumin analog A2, B3 and C1 (1 ìM) significantly degrade both $SNCA^{WT}$ or $SNCA^{A53T}$ (FIG. 8A and FIG. 8C). Notably, C1 showed the best effects on SNCA clearance. Corynoxine B (Cory B) is used as a positive control. Furthermore, the activity of C1 in degrading SNCA was significantly blocked by autophagy inhibitor wortmannin (WM) or the lysosome inhibitor CQ (FIG. 8B and FIG. 8D), indicating that C1 promotes the clearance of SNCA via autophagy-lysosome pathway.

Example VII

Figure 9A:
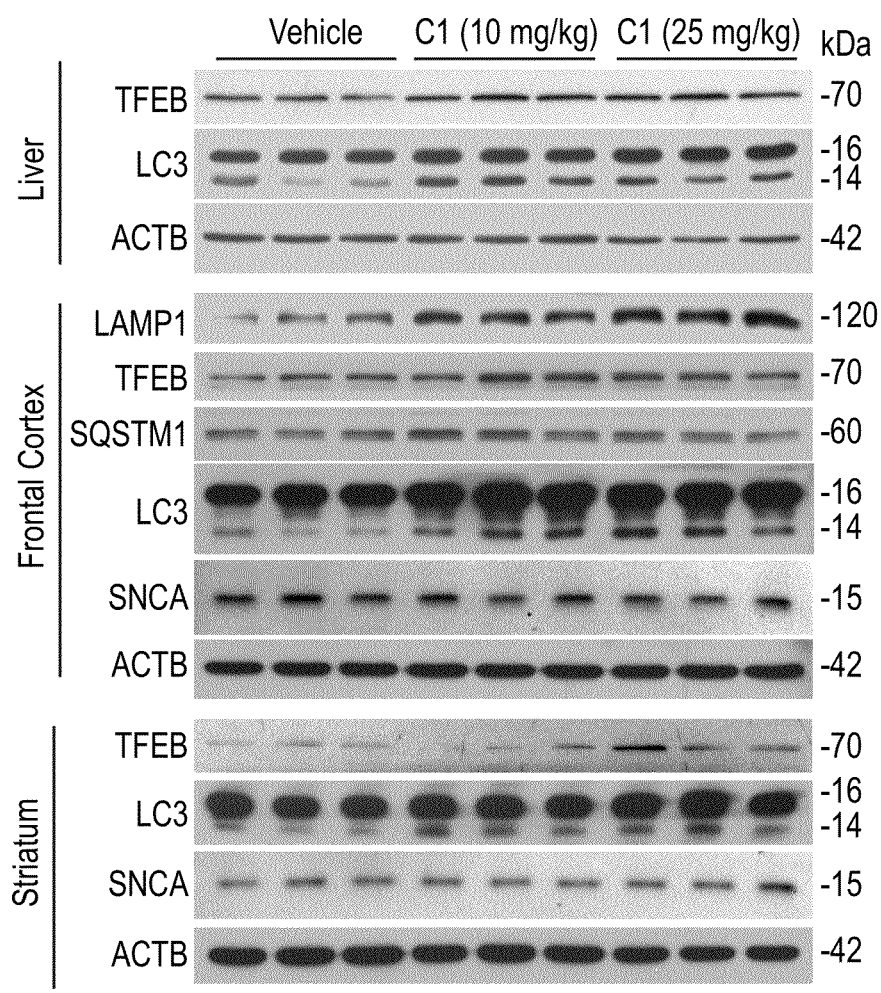
FIG. 9A shows western blots of the various protein levels as indicated in the liver, frontal cortex and striatum.
Figure 9B:
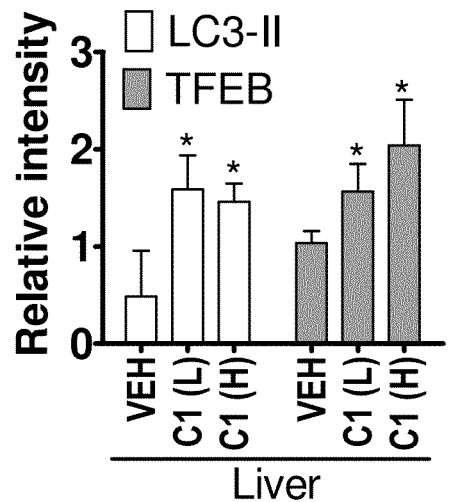
FIG. 9B-9D are bar charts showing quantitative data of various protein expressions in the liver, frontal cortex and striatum. Data are presented as the mean±SD (n=6). *p<0.05 vs. the vehicle treatment.
Figure 9C:
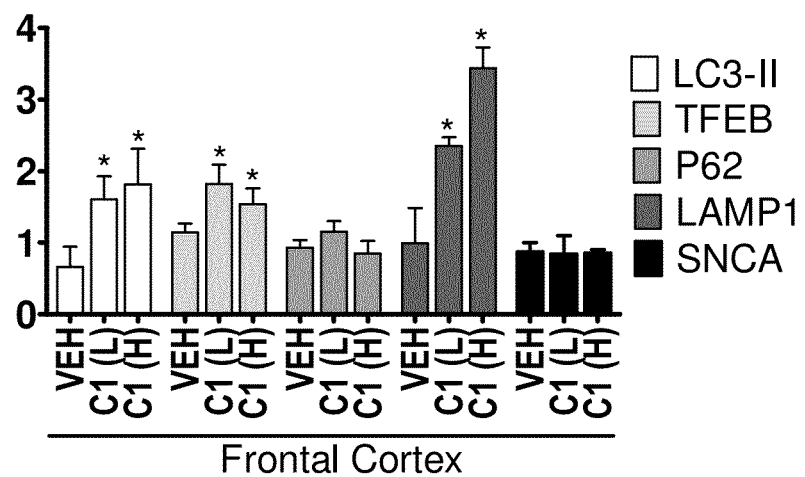
Figure 9D:
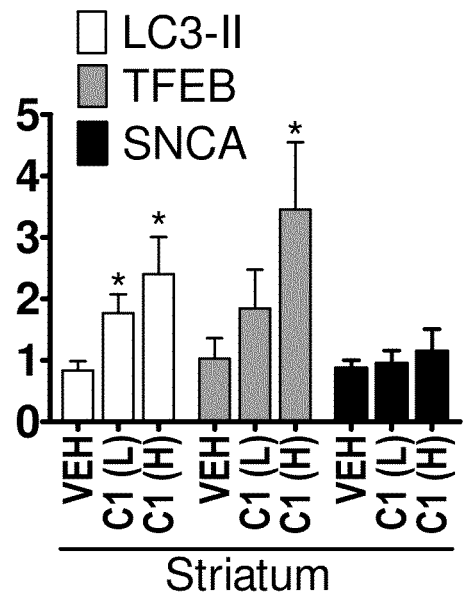
Figure 9E:
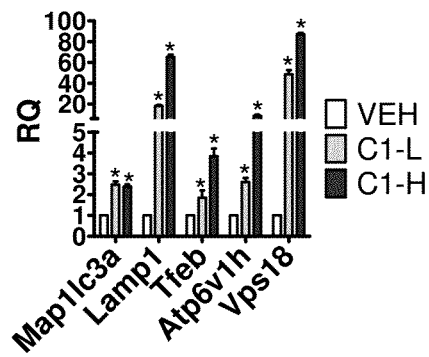
FIG. 9E shows mRNA levels in the frontal cortex were analyzed by real time PCR. Relative quantification (RQ) is presented as means±SD (n=4). *p<0.05 vs. the vehicle treatment.

Oral Administration of Curcumin Analog C1 Activates TFEB and Autophagy in Rats Brains Acute toxicity of C1 in rats by single-dose intravenous (IV) tail vein injection and the medium lethal dose ($LD_{50}$) value of C1 is 175 mg/kg are determined. Short-term oral administration of C1 (10 mg/kg and 25 mg/kg) dose-dependently increases the expression of LC3-II and TFEB in the liver, frontal cortex and striatum of the brains (FIG. 9A-D). However, short-term administration of C1 does not affect the levels of endogenous SQSTM1/p62 or SNCA in the brains (FIG. 9A-D). Moreover, C1 treatment dose-dependently increases the expression of LAMP1 in the brains. The real-time PCR analysis of brain lysates shows that C1 up-regulated TFEB and several autophagy/lysosomal genes in the brain (FIG. 9E). This indicates that C1 can pass the blood-brain barrier (BBB). The average concentration of C1 in brain tissues is 0.26±0.063 µg/g determined by HPLC after oral administration of C1 (10 mg/kg) for 6 h. Based on these data, it is demonstrated that short-term treatment of C1 can activate TFEB and autophagy in rats' brains while insufficient to degrade the autophagy substrates SQSTM1/p62 and SNCA.

MTOR pathway and TFEB translocation in the frontal cortex of rats orally administrated with C1 is shown. Consistent with the in vitro observation, C1 treatment (25 mg/kg) significantly increases the phosphorylation of MTOR and RPS6KB1 (FIG. 10A), confirming that C1 promotes MTOR activity. C1 administration dose-dependently promotes the nuclear translocation of TFEB in the brains as determined by western blot (FIG. 10B). The interaction between endogenous TFEB and MTOR is significantly inhibited in the frontal cortex of rats treated with C1 (25 mg/kg) (FIG. 10C).

Example VIII

Figure 11A:
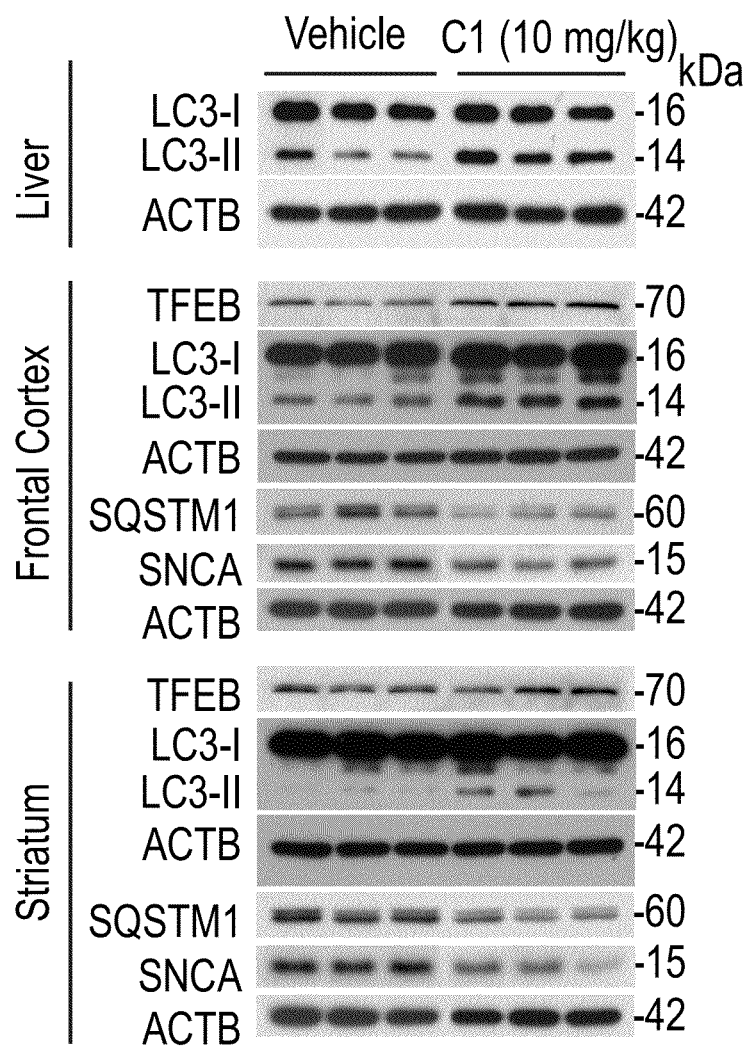
FIG. 11A is western blots showing the protein levels as indicated in the liver, frontal cortex and striatum.
Figure 11B:
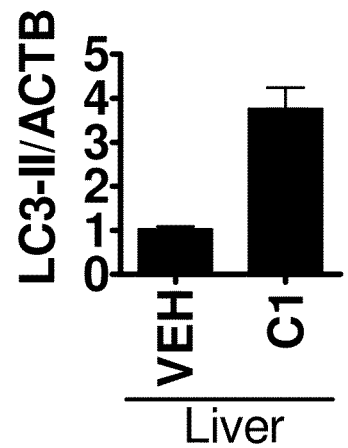
FIGS. 11B-11D are quantitative data protein levels in the liver frontal cortex and striatum. Data are presented as the mean±SD (n=6). *p<0.05 vs. the vehicle treatment.
Figure 11C:
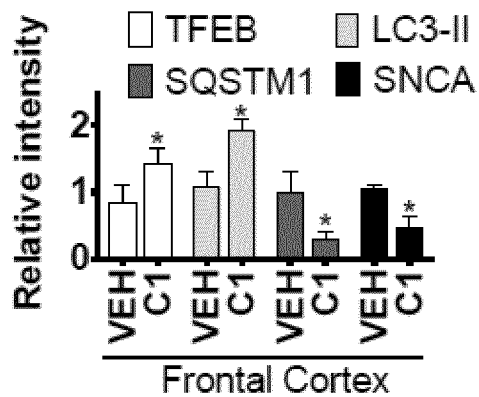
Figure 11D:
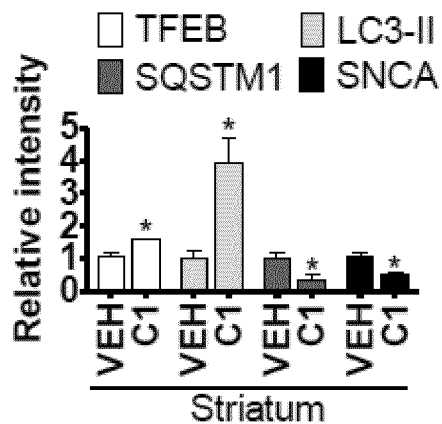

Chronic Administration of Curcumin Analog C1 Promotes the Degradation of Endogenous SNCA Rats receive oral administration of C1 (10 mg/kg) for 21 days. Another dose of C1 is given for 6 h and the average concentration of C1 in brain tissues is 0.849±0.302 µg/g. Then the autophagy markers in the livers and brains are analyzed. Chronic C1 treatment increases the levels of LC3-II in the livers (FIGS. 11A and B). In the frontal cortex and striatum of brains, C1 treatment significantly increases the levels of TFEB and LC3-II (FIGS. 11A, C and D). Notably, the levels of endogenous SQSTM1/p62 and SNCA significantly decrease in rats' brains treated with C1 for 21 days (FIGS. 11A, C and D), indicating that chronic administration of C1 is sufficient to promote autophagy-mediated degradation of protein aggregates in the brains. During the treatment procedure, no changes in body weight or behavior abnormalities are observed. Histological evaluation of major organs (liver, lungs, kidneys, and pancreas) do not reveal any morphological abnormalities.

Translation of Animal Dosage to Human Dosage.

The effective dosage of the invented curcumin mono-carbonyl analog C1 ranges from 10 mg/kg (body weight) to 175 mg/kg (body weight) per day. According to the dose translation formula (Reagan-Shaw S1, et. al., *Dose translation from animal to human studies revisited. FASEB J.* 2008; 22(3):659-61.), the effective translated human dose of the curcumin mono-carbonyl analog C1 of the present invention ranges from 1.62 mg/kg (body weight) to 28.38 mg/kg (body weight) per day.

INDUSTRIAL APPLICABILITY

The present invention discloses novel compositions comprising an autophagy enhancement compound. In particular, the present invention relates to a composition comprising a small molecule being able to enhance autophagy and lysosome biogenesis by activating the gene TFEB which can prevent the accumulation of toxic protein aggregates in treating neurodegenerative diseases such as Parkinson's, Alzheimer's and Huntington's diseases.

If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

The invention claimed is:

1. A method for enhancing autophagy in cells comprising providing a mono-carbonyl analog of curcumin having a formula of

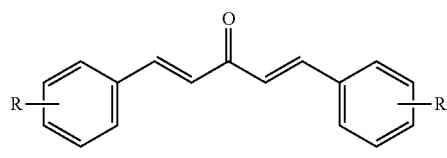

wherein R is $CF_3$ or $OCH_3$.

2. The method of claim 1, wherein said R is $CF_3$ and the mono-carbonyl analog of curcumin having a formula of A2:

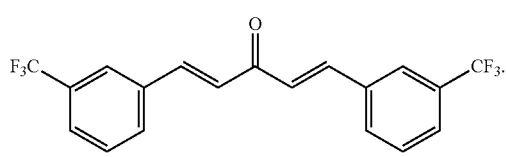

3. The method of claim 1, wherein said R is OCH$_3$ and the mono-carbonyl analog of curcumin having a formula of C1:

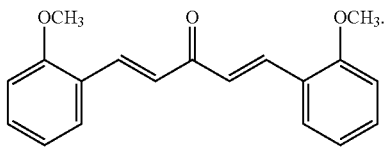

4. A method of treating neurodegenerative diseases comprising administering a composition comprising a mono-carbonyl analog of curcumin having a formula of

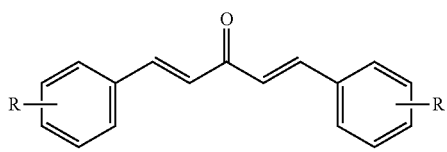

wherein R is CF$_3$ or OCH$_3$ to a subject in need thereof.

5. The method according to claim 4, wherein the neurodegenerative diseases comprising Alzheimer's disease, Parkinson's disease, Huntington's disease and Creutzfeldt-Jakob disease.

6. The method according to claim 4, wherein the mono-carbonyl analog is

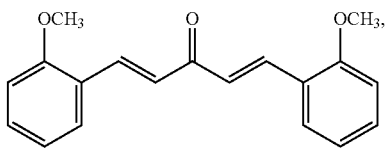

the mono-carbonyl analogs is administered at 1.62 mg/kg to 28.38 mg/kg body weight of the subject in need thereof.

7. A method of enhancing lysosome biogenesis in cells comprising providing a mono-carbonyl analog of curcumin having a formula of

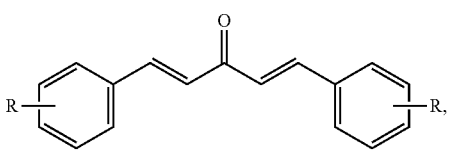

wherein R is CF$_3$ or OCH$_3$.

8. The method of claim 7, wherein the mono-carbonyl analog of curcumin comprises a formula of C1:

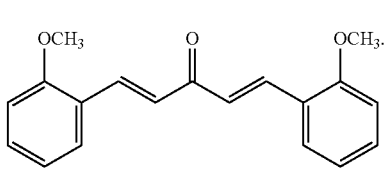

9. The method of claim 7, wherein the cells are neuronal cells.

10. The method of claim 7, wherein the cells are non-neuronal cells.

11. The method of claim 7, wherein said R is CF$_3$ and the mono-carbonyl analog of curcumin having a formula of A2:

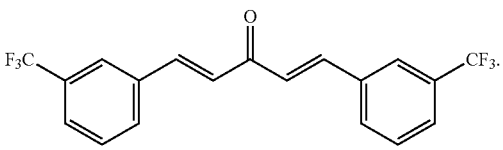

12. The method of claim 7, wherein said providing includes administrating the mono-carbonyl analog of curcumin to a subject in need thereof to treat neurodegenerative diseases.

13. The method according to claim 12, wherein the neurodegenerative diseases comprising Alzheimer's disease, Parkinson's disease, Huntington's disease and Creutzfeldt-Jakob disease.

14. The method according to claim 12, wherein the mono-carbonyl analog is

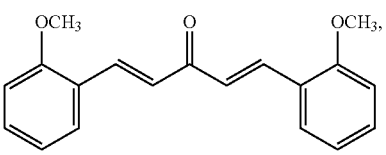

the mono-carbonyl analogs is administered at 1.62 mg/kg to 28.38 mg/kg body weight of the subject in need thereof.

15. The method according to claim 12, wherein the composition is administered to the subject in need thereof via oral administration, intravenous injection or both.

16. The method according to claim 12, wherein said R is CF$_3$ and the mono-carbonyl analog of curcumin comprises a formula of A2:

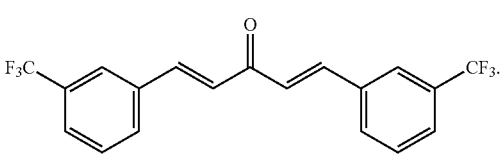

17. The method according to claim 12, wherein said R is OCH$_3$ and the mono-carbonyl analog of curcumin comprises a formula of C1:

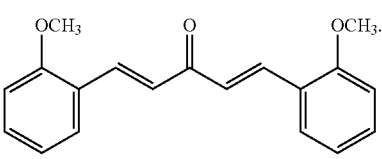

* * * * *

SEQUENCE LISTING

```
<160> NUMBER OF SEQ ID NOS: 80

<210> SEQ ID NO 1
<211> LENGTH: 22
<212> TYPE: DNA
<213> ORGANISM: Artificial Sequence
<220> FEATURE:
<223> OTHER INFORMATION: ATG9B Forward Primer Human

<400> SEQUENCE: 1
accctgtcag atgccatcct ac                                            22

<210> SEQ ID NO 2
<211> LENGTH: 22
<212> TYPE: DNA
<213> ORGANISM: Artificial Sequence
<220> FEATURE:
<223> OTHER INFORMATION: ATG9B Reverse Primer Human

<400> SEQUENCE: 2
ccagtagctg aagaggttgc ag                                            22

<210> SEQ ID NO 3
<211> LENGTH: 23
<212> TYPE: DNA
<213> ORGANISM: Artificial Sequence
<220> FEATURE:
<223> OTHER INFORMATION: ATG10 Forward Primer Human

<400> SEQUENCE: 3
```

```
ggtgatagtt gggaatggag acc                                          23

<210> SEQ ID NO 4
<211> LENGTH: 22
<212> TYPE: DNA
<213> ORGANISM: Artificial Sequence
<220> FEATURE:
<223> OTHER INFORMATION: ATG10 Reverse Primer Human

<400> SEQUENCE: 4
gtctgtccat gggtagatgc tc                                           22

<210> SEQ ID NO 5
<211> LENGTH: 22
<212> TYPE: DNA
<213> ORGANISM: Artificial Sequence
<220> FEATURE:
<223> OTHER INFORMATION: ATG16L1 Forward Primer Human

<400> SEQUENCE: 5
ctacggaaga gaaccaggag ct                                           22

<210> SEQ ID NO 6
<211> LENGTH: 22
<212> TYPE: DNA
<213> ORGANISM: Artificial Sequence
<220> FEATURE:
<223> OTHER INFORMATION: ATG16L1 Reverse Primer Human

<400> SEQUENCE: 6
ctggtagagg ttcctttgct gc                                           22

<210> SEQ ID NO 7
<211> LENGTH: 22
<212> TYPE: DNA
<213> ORGANISM: Artificial Sequence
<220> FEATURE:
<223> OTHER INFORMATION: BCL2 Forward Primer Human

<400> SEQUENCE: 7
atcgccctgt ggatgactga gt                                           22

<210> SEQ ID NO 8
<211> LENGTH: 23
<212> TYPE: DNA
<213> ORGANISM: Artificial Sequence
<220> FEATURE:
<223> OTHER INFORMATION: BCL2 Reverse Primer Human

<400> SEQUENCE: 8
gccaggagaa atcaaacaga ggc                                          23

<210> SEQ ID NO 9
<211> LENGTH: 22
<212> TYPE: DNA
<213> ORGANISM: Artificial Sequence
<220> FEATURE:
<223> OTHER INFORMATION: CLN3 Forward Primer Human

<400> SEQUENCE: 9
gaacacttcc ctgagtcacg ct                                           22

<210> SEQ ID NO 10
<211> LENGTH: 22
<212> TYPE: DNA
<213> ORGANISM: Artificial Sequence
```

```
<220> FEATURE:
<223> OTHER INFORMATION: CLN3 Reverse Primer Human

<400> SEQUENCE: 10
aggtgaaacg gatgcgacag ca                                               22

<210> SEQ ID NO 11
<211> LENGTH: 23
<212> TYPE: DNA
<213> ORGANISM: Artificial Sequence
<220> FEATURE:
<223> OTHER INFORMATION: GABARAPL1 Forward Primer Human

<400> SEQUENCE: 11
ttgtagagaa ggctccaaaa gcc                                              23

<210> SEQ ID NO 12
<211> LENGTH: 22
<212> TYPE: DNA
<213> ORGANISM: Artificial Sequence
<220> FEATURE:
<223> OTHER INFORMATION: GABARAPL1 Reverse Primer Human

<400> SEQUENCE: 12
ggtctcaggt ggattctctt cc                                               22

<210> SEQ ID NO 13
<211> LENGTH: 22
<212> TYPE: DNA
<213> ORGANISM: Artificial Sequence
<220> FEATURE:
<223> OTHER INFORMATION: GABARAPL2 Forward Primer Human

<400> SEQUENCE: 13
ccagcttcct tctgaaaagg cg                                               22

<210> SEQ ID NO 14
<211> LENGTH: 22
<212> TYPE: DNA
<213> ORGANISM: Artificial Sequence
<220> FEATURE:
<223> OTHER INFORMATION: GABARAPL2 Reverse Primer Human

<400> SEQUENCE: 14
ttctctccgc tgtaggccac at                                               22

<210> SEQ ID NO 15
<211> LENGTH: 22
<212> TYPE: DNA
<213> ORGANISM: Artificial Sequence
<220> FEATURE:
<223> OTHER INFORMATION: MAP1LC3B Forward Primer Human

<400> SEQUENCE: 15
gagaagcagc ttcctgttct gg                                               22

<210> SEQ ID NO 16
<211> LENGTH: 22
<212> TYPE: DNA
<213> ORGANISM: Artificial Sequence
<220> FEATURE:
<223> OTHER INFORMATION: MAP1LC3B Reverse Primer Human

<400> SEQUENCE: 16
gtgtccgttc accaacagga ag                                               22
```

<210> SEQ ID NO 17
<211> LENGTH: 22
<212> TYPE: DNA
<213> ORGANISM: Artificial Sequence
<220> FEATURE:
<223> OTHER INFORMATION: MAPK14 Forward Primer Human

<400> SEQUENCE: 17
gagcgttacc agaacctgtc tc                                            22

<210> SEQ ID NO 18
<211> LENGTH: 23
<212> TYPE: DNA
<213> ORGANISM: Artificial Sequence
<220> FEATURE:
<223> OTHER INFORMATION: MAPK14 Reverse Primer Human

<400> SEQUENCE: 18
agtaaccgca gttctctgta ggt                                           23

<210> SEQ ID NO 19
<211> LENGTH: 22
<212> TYPE: DNA
<213> ORGANISM: Artificial Sequence
<220> FEATURE:
<223> OTHER INFORMATION: SQSTM1 Forward Primer Human

<400> SEQUENCE: 19
tgtgtagcgt ctgcgaggga aa                                            22

<210> SEQ ID NO 20
<211> LENGTH: 22
<212> TYPE: DNA
<213> ORGANISM: Artificial Sequence
<220> FEATURE:
<223> OTHER INFORMATION: SQSTM1 Reverse Primer Human

<400> SEQUENCE: 20
agtgtccgtg tttcaccttc cg                                            22

<210> SEQ ID NO 21
<211> LENGTH: 23
<212> TYPE: DNA
<213> ORGANISM: Artificial Sequence
<220> FEATURE:
<223> OTHER INFORMATION: VPS11 Forward Primer Human

<400> SEQUENCE: 21
gctataccaa gctcaaggac agc                                           23

<210> SEQ ID NO 22
<211> LENGTH: 22
<212> TYPE: DNA
<213> ORGANISM: Artificial Sequence
<220> FEATURE:
<223> OTHER INFORMATION: VPS11 Reverse Primer Human

<400> SEQUENCE: 22
atggttctcc gccagataca gg                                            22

<210> SEQ ID NO 23
<211> LENGTH: 22
<212> TYPE: DNA
<213> ORGANISM: Artificial Sequence
<220> FEATURE:
<223> OTHER INFORMATION: VPS18 Forward Primer Human

```
<400> SEQUENCE: 23
acttgggcaa ggcaaatgag cc                                              22

<210> SEQ ID NO 24
<211> LENGTH: 23
<212> TYPE: DNA
<213> ORGANISM: Artificial Sequence
<220> FEATURE:
<223> OTHER INFORMATION: VPS18 Reverse Primer Human

<400> SEQUENCE: 24
ccttctgtcc atttcggttc acg                                             23

<210> SEQ ID NO 25
<211> LENGTH: 22
<212> TYPE: DNA
<213> ORGANISM: Artificial Sequence
<220> FEATURE:
<223> OTHER INFORMATION: WIPI1 Forward Primer Human

<400> SEQUENCE: 25
cttcaagctg gaacaggtca cc                                              22

<210> SEQ ID NO 26
<211> LENGTH: 22
<212> TYPE: DNA
<213> ORGANISM: Artificial Sequence
<220> FEATURE:
<223> OTHER INFORMATION: WIPI1 Reverse Primer Human

<400> SEQUENCE: 26
cggagaagtt caagcgtgca gt                                              22

<210> SEQ ID NO 27
<211> LENGTH: 22
<212> TYPE: DNA
<213> ORGANISM: Artificial Sequence
<220> FEATURE:
<223> OTHER INFORMATION: CLCN7 Forward Primer Human

<400> SEQUENCE: 27
cacagttgcc ttcgtgctga tc                                              22

<210> SEQ ID NO 28
<211> LENGTH: 22
<212> TYPE: DNA
<213> ORGANISM: Artificial Sequence
<220> FEATURE:
<223> OTHER INFORMATION: CLCN7 Reverse Primer Human

<400> SEQUENCE: 28
tggagttgta ctcgccatct gc                                              22

<210> SEQ ID NO 29
<211> LENGTH: 22
<212> TYPE: DNA
<213> ORGANISM: Artificial Sequence
<220> FEATURE:
<223> OTHER INFORMATION: ATP6V0E1 Forward Primer Human

<400> SEQUENCE: 29
ggtgacctgt tcagtttgct gc                                              22

<210> SEQ ID NO 30
```

-continued

<211> LENGTH: 23
<212> TYPE: DNA
<213> ORGANISM: Artificial Sequence
<220> FEATURE:
<223> OTHER INFORMATION: ATP6V0E1 Reverse Primer Human

<400> SEQUENCE: 30
gagcatgtct tcttcctcaa ggc                                           23

<210> SEQ ID NO 31
<211> LENGTH: 22
<212> TYPE: DNA
<213> ORGANISM: Artificial Sequence
<220> FEATURE:
<223> OTHER INFORMATION: ATP6V1H Forward Primer Human

<400> SEQUENCE: 31
cgggtcaatg agtaccgctt tg                                            22

<210> SEQ ID NO 32
<211> LENGTH: 23
<212> TYPE: DNA
<213> ORGANISM: Artificial Sequence
<220> FEATURE:
<223> OTHER INFORMATION: ATP6V1H Reverse Primer Human

<400> SEQUENCE: 32
gatactggag ctgaaagcca cac                                           23

<210> SEQ ID NO 33
<211> LENGTH: 22
<212> TYPE: DNA
<213> ORGANISM: Artificial Sequence
<220> FEATURE:
<223> OTHER INFORMATION: CTSA Forward Primer Human

<400> SEQUENCE: 33
gcttcgtgaa ggagttctcc ca                                            22

<210> SEQ ID NO 34
<211> LENGTH: 22
<212> TYPE: DNA
<213> ORGANISM: Artificial Sequence
<220> FEATURE:
<223> OTHER INFORMATION: CTSA Reverse Primer Human

<400> SEQUENCE: 34
ctgtggtcat cagtatggct gc                                            22

<210> SEQ ID NO 35
<211> LENGTH: 22
<212> TYPE: DNA
<213> ORGANISM: Artificial Sequence
<220> FEATURE:
<223> OTHER INFORMATION: CTSB Forward Primer Human

<400> SEQUENCE: 35
gcttcgatgc acgggaacaa tg                                            22

<210> SEQ ID NO 36
<211> LENGTH: 22
<212> TYPE: DNA
<213> ORGANISM: Artificial Sequence
<220> FEATURE:
<223> OTHER INFORMATION: CTSB Reverse Primer Human

<400> SEQUENCE: 36

```
cattggtgtg gatgcagatc cg                                              22
```

<210> SEQ ID NO 37
<211> LENGTH: 22
<212> TYPE: DNA
<213> ORGANISM: Artificial Sequence
<220> FEATURE:
<223> OTHER INFORMATION: CTSD Forward Primer Human

<400> SEQUENCE: 37

```
gcaaactgct ggacatcgct tg                                              22
```

<210> SEQ ID NO 38
<211> LENGTH: 23
<212> TYPE: DNA
<213> ORGANISM: Artificial Sequence
<220> FEATURE:
<223> OTHER INFORMATION: CTSD Reverse Primer Human

<400> SEQUENCE: 38

```
gccatagtgg atgtcaaacg agg                                             23
```

<210> SEQ ID NO 39
<211> LENGTH: 22
<212> TYPE: DNA
<213> ORGANISM: Artificial Sequence
<220> FEATURE:
<223> OTHER INFORMATION: CTSS Forward Primer Human

<400> SEQUENCE: 39

```
tggatcacca ctggcatctc tg                                              22
```

<210> SEQ ID NO 40
<211> LENGTH: 22
<212> TYPE: DNA
<213> ORGANISM: Artificial Sequence
<220> FEATURE:
<223> OTHER INFORMATION: CTSS Reverse Primer Human

<400> SEQUENCE: 40

```
gctccaggtt gtgaagcatc ac                                              22
```

<210> SEQ ID NO 41
<211> LENGTH: 22
<212> TYPE: DNA
<213> ORGANISM: Artificial Sequence
<220> FEATURE:
<223> OTHER INFORMATION: GALNS Forward Primer Human

<400> SEQUENCE: 41

```
agcagaccac gtttgaagga gg                                              22
```

<210> SEQ ID NO 42
<211> LENGTH: 22
<212> TYPE: DNA
<213> ORGANISM: Artificial Sequence
<220> FEATURE:
<223> OTHER INFORMATION: GALNS Reverse Primer Human

<400> SEQUENCE: 42

```
gtggtgaaga ggtccatgat gc                                              22
```

<210> SEQ ID NO 43
<211> LENGTH: 22
<212> TYPE: DNA

```
<213> ORGANISM: Artificial Sequence
<220> FEATURE:
<223> OTHER INFORMATION: GBA Forward Primer Human

<400> SEQUENCE: 43
tgctgctctc aacatccttg cc                                              22

<210> SEQ ID NO 44
<211> LENGTH: 22
<212> TYPE: DNA
<213> ORGANISM: Artificial Sequence
<220> FEATURE:
<223> OTHER INFORMATION: GBA Reverse Primer Human

<400> SEQUENCE: 44
taggtgcgga tggagaagtc ac                                              22

<210> SEQ ID NO 45
<211> LENGTH: 22
<212> TYPE: DNA
<213> ORGANISM: Artificial Sequence
<220> FEATURE:
<223> OTHER INFORMATION: GLA Forward Primer Human

<400> SEQUENCE: 45
gcaaccttga ctgccaggaa ga                                              22

<210> SEQ ID NO 46
<211> LENGTH: 23
<212> TYPE: DNA
<213> ORGANISM: Artificial Sequence
<220> FEATURE:
<223> OTHER INFORMATION: GLA Reverse Primer Human

<400> SEQUENCE: 46
ctcataacct gcatccttcc agc                                             23

<210> SEQ ID NO 47
<211> LENGTH: 22
<212> TYPE: DNA
<213> ORGANISM: Artificial Sequence
<220> FEATURE:
<223> OTHER INFORMATION: GNS Forward Primer Human

<400> SEQUENCE: 47
tccactgttg gttcgaggac ct                                              22

<210> SEQ ID NO 48
<211> LENGTH: 22
<212> TYPE: DNA
<213> ORGANISM: Artificial Sequence
<220> FEATURE:
<223> OTHER INFORMATION: GNS Reverse Primer Human

<400> SEQUENCE: 48
taggtcgtag ccagcaatgt cc                                              22

<210> SEQ ID NO 49
<211> LENGTH: 22
<212> TYPE: DNA
<213> ORGANISM: Artificial Sequence
<220> FEATURE:
<223> OTHER INFORMATION: HEXA Forward Primer Human

<400> SEQUENCE: 49
ggaggtcatt gaatacgcac gg                                              22
```

<210> SEQ ID NO 50
<211> LENGTH: 22
<212> TYPE: DNA
<213> ORGANISM: Artificial Sequence
<220> FEATURE:
<223> OTHER INFORMATION: HEXA Reverse Primer Human

<400> SEQUENCE: 50
ggattcactg gtccaaaggt gc                                              22

<210> SEQ ID NO 51
<211> LENGTH: 22
<212> TYPE: DNA
<213> ORGANISM: Artificial Sequence
<220> FEATURE:
<223> OTHER INFORMATION: LAMP1 Forward Primer Human

<400> SEQUENCE: 51
cgtgtcacga aggcgttttc ag                                              22

<210> SEQ ID NO 52
<211> LENGTH: 22
<212> TYPE: DNA
<213> ORGANISM: Artificial Sequence
<220> FEATURE:
<223> OTHER INFORMATION: LAMP1 Reverse Primer Human

<400> SEQUENCE: 52
ctgttctcgt ccagcagaca ct                                              22

<210> SEQ ID NO 53
<211> LENGTH: 22
<212> TYPE: DNA
<213> ORGANISM: Artificial Sequence
<220> FEATURE:
<223> OTHER INFORMATION: MCOLN1 Forward Primer Human

<400> SEQUENCE: 53
cggactgcta taccttcagc gt                                              22

<210> SEQ ID NO 54
<211> LENGTH: 22
<212> TYPE: DNA
<213> ORGANISM: Artificial Sequence
<220> FEATURE:
<223> OTHER INFORMATION: MCOLN1 Reverse Primer Human

<400> SEQUENCE: 54
ggtgcttaca ctcctggatg tg                                              22

<210> SEQ ID NO 55
<211> LENGTH: 22
<212> TYPE: DNA
<213> ORGANISM: Artificial Sequence
<220> FEATURE:
<223> OTHER INFORMATION: PSAP Forward Primer Human

<400> SEQUENCE: 55
gcctccaaga atgtcatccc tg                                              22

<210> SEQ ID NO 56
<211> LENGTH: 23
<212> TYPE: DNA
<213> ORGANISM: Artificial Sequence
<220> FEATURE:

-continued

<223> OTHER INFORMATION: PSAP Reverse Primer Human

<400> SEQUENCE: 56
caatcagctt ggtcacctcc ttc                                   23

<210> SEQ ID NO 57
<211> LENGTH: 22
<212> TYPE: DNA
<213> ORGANISM: Artificial Sequence
<220> FEATURE:
<223> OTHER INFORMATION: SCPEP1 Forward Primer Human

<400> SEQUENCE: 57
cattcagcga gggaccatca ag                                    22

<210> SEQ ID NO 58
<211> LENGTH: 22
<212> TYPE: DNA
<213> ORGANISM: Artificial Sequence
<220> FEATURE:
<223> OTHER INFORMATION: SCPEP1 Reverse Primer Human

<400> SEQUENCE: 58
cctctgccag acctttgtct tc                                    22

<210> SEQ ID NO 59
<211> LENGTH: 22
<212> TYPE: DNA
<213> ORGANISM: Artificial Sequence
<220> FEATURE:
<223> OTHER INFORMATION: SGSH Forward Primer Human

<400> SEQUENCE: 59
aatgccttca cctcggtcag ca                                    22

<210> SEQ ID NO 60
<211> LENGTH: 23
<212> TYPE: DNA
<213> ORGANISM: Artificial Sequence
<220> FEATURE:
<223> OTHER INFORMATION: SGSH Reverse Primer Human

<400> SEQUENCE: 60
tgtcgaagga gttgaagtgg tgc                                   23

<210> SEQ ID NO 61
<211> LENGTH: 22
<212> TYPE: DNA
<213> ORGANISM: Artificial Sequence
<220> FEATURE:
<223> OTHER INFORMATION: TFEB Forward Primer Human

<400> SEQUENCE: 61
cctggagatg accaacaagc ag                                    22

<210> SEQ ID NO 62
<211> LENGTH: 22
<212> TYPE: DNA
<213> ORGANISM: Artificial Sequence
<220> FEATURE:
<223> OTHER INFORMATION: TFEB Reverse Primer Human

<400> SEQUENCE: 62
taggcagctc ctgcttcacc ac                                    22

```
<210> SEQ ID NO 63
<211> LENGTH: 22
<212> TYPE: DNA
<213> ORGANISM: Artificial Sequence
<220> FEATURE:
<223> OTHER INFORMATION: TPP1 Forward Primer Human

<400> SEQUENCE: 63
ggtggcttca gcaatgtgtt cc                                          22

<210> SEQ ID NO 64
<211> LENGTH: 22
<212> TYPE: DNA
<213> ORGANISM: Artificial Sequence
<220> FEATURE:
<223> OTHER INFORMATION: TPP1 Reverse Primer Human

<400> SEQUENCE: 64
gaagtaactg gatggtggca gg                                          22

<210> SEQ ID NO 65
<211> LENGTH: 23
<212> TYPE: DNA
<213> ORGANISM: Artificial Sequence
<220> FEATURE:
<223> OTHER INFORMATION: TMEM55B Forward Primer Human

<400> SEQUENCE: 65
cagagttcac agaccgcact ttg                                         23

<210> SEQ ID NO 66
<211> LENGTH: 22
<212> TYPE: DNA
<213> ORGANISM: Artificial Sequence
<220> FEATURE:
<223> OTHER INFORMATION: TMEM55B Reverse Primer Human

<400> SEQUENCE: 66
ggcagtgact gccaaaagca ag                                          22

<210> SEQ ID NO 67
<211> LENGTH: 22
<212> TYPE: DNA
<213> ORGANISM: Artificial Sequence
<220> FEATURE:
<223> OTHER INFORMATION: GAPDH Forward Primer Human

<400> SEQUENCE: 67
gtctcctctg acttcaacag cg                                          22

<210> SEQ ID NO 68
<211> LENGTH: 22
<212> TYPE: DNA
<213> ORGANISM: Artificial Sequence
<220> FEATURE:
<223> OTHER INFORMATION: GAPDH Reverse Primer Human

<400> SEQUENCE: 68
accaccctgt tgctgtagcc aa                                          22

<210> SEQ ID NO 69
<211> LENGTH: 22
<212> TYPE: DNA
<213> ORGANISM: Artificial Sequence
<220> FEATURE:
<223> OTHER INFORMATION: Map1lc3a Forward Primer Rat
```

<400> SEQUENCE: 69
aacaggagaa ggatgaagac gg                                           22

<210> SEQ ID NO 70
<211> LENGTH: 22
<212> TYPE: DNA
<213> ORGANISM: Artificial Sequence
<220> FEATURE:
<223> OTHER INFORMATION: Map1lc3a Reverse Primer Rat

<400> SEQUENCE: 70
ttgactcaga agccgaaggt tt                                           22

<210> SEQ ID NO 71
<211> LENGTH: 22
<212> TYPE: DNA
<213> ORGANISM: Artificial Sequence
<220> FEATURE:
<223> OTHER INFORMATION: Lamp1 Forward Primer Rat

<400> SEQUENCE: 71
gcacctccaa ctattccctg aa                                           22

<210> SEQ ID NO 72
<211> LENGTH: 22
<212> TYPE: DNA
<213> ORGANISM: Artificial Sequence
<220> FEATURE:
<223> OTHER INFORMATION: Lamp1 Reverse Primer Rat

<400> SEQUENCE: 72
acagacccaa acctgtcact tt                                           22

<210> SEQ ID NO 73
<211> LENGTH: 22
<212> TYPE: DNA
<213> ORGANISM: Artificial Sequence
<220> FEATURE:
<223> OTHER INFORMATION: Tfeb Forward Primer Rat

<400> SEQUENCE: 73
aatgggagca accgtactta gg                                           22

<210> SEQ ID NO 74
<211> LENGTH: 22
<212> TYPE: DNA
<213> ORGANISM: Artificial Sequence
<220> FEATURE:
<223> OTHER INFORMATION: Tfeb Reverse Primer Rat

<400> SEQUENCE: 74
gagggaagac aggtccatga ag                                           22

<210> SEQ ID NO 75
<211> LENGTH: 22
<212> TYPE: DNA
<213> ORGANISM: Artificial Sequence
<220> FEATURE:
<223> OTHER INFORMATION: Atp6v1h Forward Primer Rat

<400> SEQUENCE: 75
ctcagtatgt gcagtgtgtt gc                                           22

<210> SEQ ID NO 76
<211> LENGTH: 22

```
<212> TYPE: DNA
<213> ORGANISM: Artificial Sequence
<220> FEATURE:
<223> OTHER INFORMATION: Atp6v1h Reverse Primer Rat

<400> SEQUENCE: 76
tacagttcac cccatctgct tc                                              22

<210> SEQ ID NO 77
<211> LENGTH: 22
<212> TYPE: DNA
<213> ORGANISM: Artificial Sequence
<220> FEATURE:
<223> OTHER INFORMATION: Vps18 Forward Primer Rat

<400> SEQUENCE: 77
gctgatgatt cgctccattg ac                                              22

<210> SEQ ID NO 78
<211> LENGTH: 22
<212> TYPE: DNA
<213> ORGANISM: Artificial Sequence
<220> FEATURE:
<223> OTHER INFORMATION: Vps18 Reverse Primer Rat

<400> SEQUENCE: 78
agtctggtag ctgtatccct gt                                              22

<210> SEQ ID NO 79
<211> LENGTH: 22
<212> TYPE: DNA
<213> ORGANISM: Artificial Sequence
<220> FEATURE:
<223> OTHER INFORMATION: Actb Forward Primer Rat

<400> SEQUENCE: 79
ctgtgtggat tggtggctct at                                              22

<210> SEQ ID NO 80
<211> LENGTH: 22
<212> TYPE: DNA
<213> ORGANISM: Artificial Sequence
<220> FEATURE:
<223> OTHER INFORMATION: Actb Reverse Primer Rat

<400> SEQUENCE: 80
gtaacagtcc gcctagaagc at                                              22
```